(12) United States Patent
Ahmed et al.

(10) Patent No.: US 11,285,148 B1
(45) Date of Patent: Mar. 29, 2022

(54) KETOCONAZOLE OPHTHALMIC PREPARATIONS CONTAINING TRANS-ETHOSOMAL DRUG NANOPARTICLES

(71) Applicant: King Abdulaziz University, Jeddah (SA)

(72) Inventors: Tarek A. Ahmed, Jeddah (SA); Maram M. Alzahrani, Jeddah (SA); Nabil A. Alhakamy, Jeddah (SA); Raed I. Felimban, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/383,516

(22) Filed: Jul. 23, 2021

(51) Int. Cl.
| | | |
|---|---|---|
| *A61K 31/496* | (2006.01) |
| *A61K 9/127* | (2006.01) |
| *A61K 9/00* | (2006.01) |
| *A61K 47/10* | (2017.01) |
| *A61P 31/10* | (2006.01) |
| *A61K 9/06* | (2006.01) |
| *A61K 47/24* | (2006.01) |
| *A61K 47/18* | (2017.01) |
| *A61K 47/12* | (2006.01) |
| *A61K 47/38* | (2006.01) |
| *A61K 47/26* | (2006.01) |

(52) U.S. Cl.
CPC .......... *A61K 31/496* (2013.01); *A61K 9/0048* (2013.01); *A61K 9/06* (2013.01); *A61K 9/127* (2013.01); *A61K 47/10* (2013.01); *A61K 47/12* (2013.01); *A61K 47/18* (2013.01); *A61K 47/24* (2013.01); *A61K 47/26* (2013.01); *A61K 47/38* (2013.01); *A61P 31/10* (2018.01)

(58) Field of Classification Search
CPC .... A61P 3/10; A61P 35/00; A61P 9/10; A61P 13/12; A61P 3/04; A61P 9/14; A61P 3/06; A61P 19/02; A61P 27/02; A61P 11/02; A61P 15/10; A61P 17/02; A61P 25/00; A61P 29/00; A61P 7/00; A61P 9/00; A61P 19/00; A61P 19/08; A61P 31/00; A61P 43/00; A61P 5/48; A61P 11/06; A61P 1/04; A61P 31/04; A61P 39/00; A61P 3/00; A61K 38/00; A61K 38/18; A61K 38/39; A61K 31/44; A61K 31/50; A61K 38/53; A61K 41/0061; A61K 49/0052; A61K 2800/412; A61K 2800/5426; A61K 2800/75; A61K 31/4045; A61K 31/5025; A61K 31/519; A61K 31/727; A61K 36/53; A61K 36/886; A61K 38/16; A61K 38/1709; A61K 38/26; A61K 47/542; A61K 47/554; A61K 49/0423; A61K 8/062; A61K 8/11; A61K 8/9789; A61K 8/9794; A61K 9/0053; A61K 31/137; A61K 47/10; A61K 49/0438; A61K 2300/00; A61K 31/439; A61K 47/18; A61K 47/46; A61K 31/506; A61K 45/06; A61K 47/24; A61K 49/04; A61K 49/0409; A61K 49/0447; A61K 49/06; A61K 49/22; A61K 9/127; A61K 9/7007; A61K 9/7069; A61K 9/7084; A61M 2205/32; A61M 5/007
See application file for complete search history.

(56) References Cited

U.S. PATENT DOCUMENTS

| | | |
|---|---|---|
| 8,663,639 B2 | 3/2014 | Dor et al. |
| 9,351,940 B2 | 5/2016 | Salman et al. |

FOREIGN PATENT DOCUMENTS

| | | |
|---|---|---|
| AU | 2012241758 | 10/2012 |
| CN | 100418530 | 9/2008 |

OTHER PUBLICATIONS

Mohammed et al. (hereafter, "Mohammed", Transethosomes a Novel Transdermal Drug Delivery System for Antifungal Drugs, International Journal of Drug Delivery Technology, 2021; 11(1): 238-243). (Year: 2021).*

El-Enin et al., "Proniosomal gel-mediated topical delivery of fluconazole:Development, in vitro characterization, and microbiologicalevaluation", J Adv Pharm Technol Res. Jan.-Mar. 2019; 10(1): 20-26.

Abdelbary et al., "Ocular ketoconazole-loaded proniosomal gels: formulation, ex vivo corneal permeation and in vivo studies" (2017) Drug Delivery, 24:1, 309-319.

* cited by examiner

*Primary Examiner* — Audrea B Coniglio
(74) *Attorney, Agent, or Firm* — WC&F IP

(57) ABSTRACT

An ophthalmic formulation comprising transethosomes is provided. The transethosomes include a phospholipid, an edge activator, ethanol, and ketoconazole, wherein a surface of the transethosome is modified with a cationic charge inducing agent. The transethosomes may be incorporated into in situ gelling or hydrogel compositions. The formulations are useful for the sustained delivery of ketoconazole to the posterior eye segment of a subject.

16 Claims, 15 Drawing Sheets

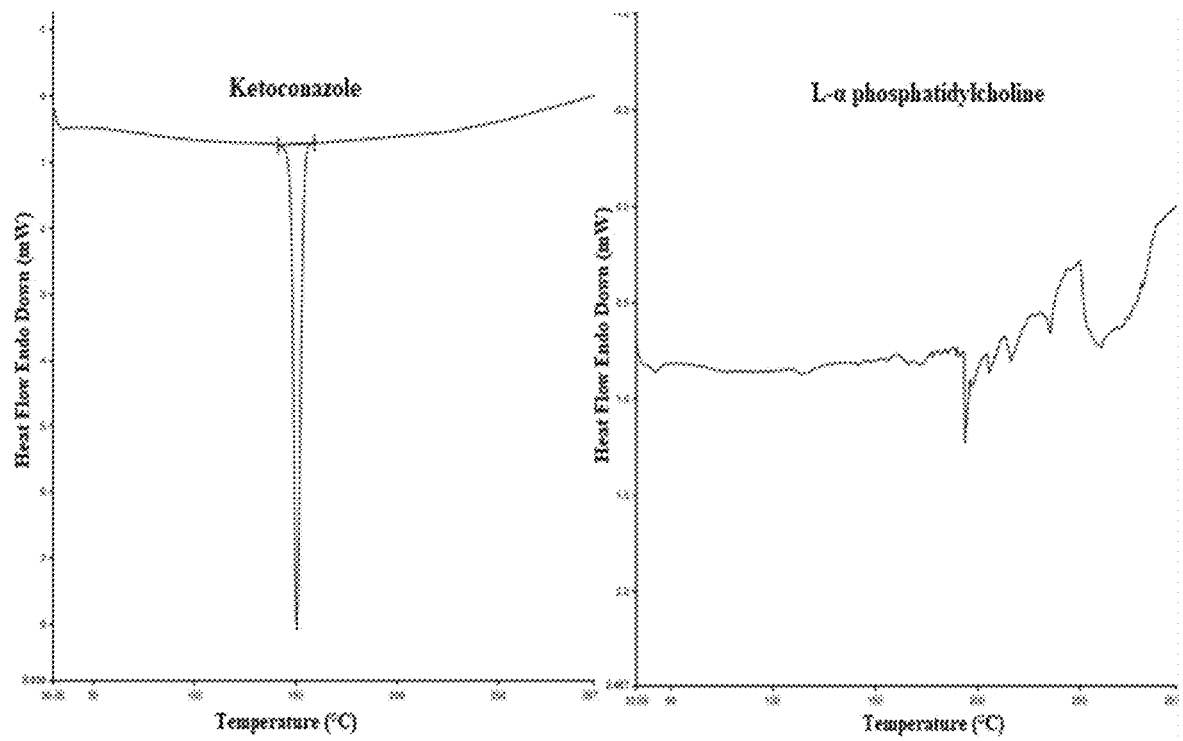
FIG. 7A
FIG. 7B
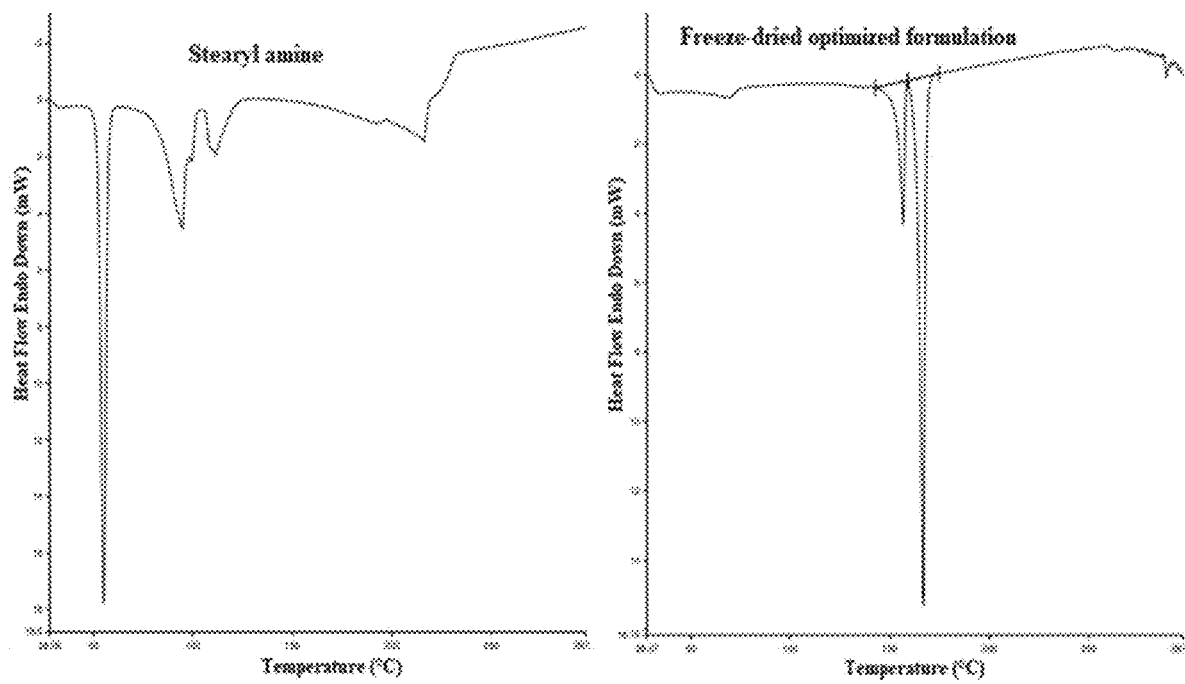
FIG. 7C
FIG. 7D

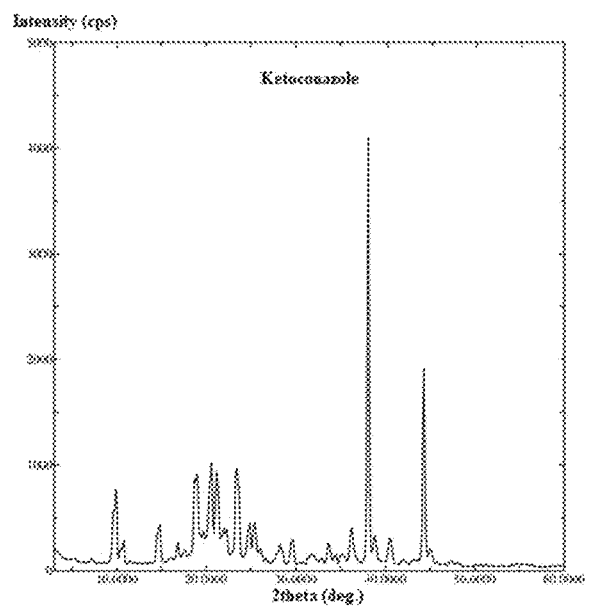 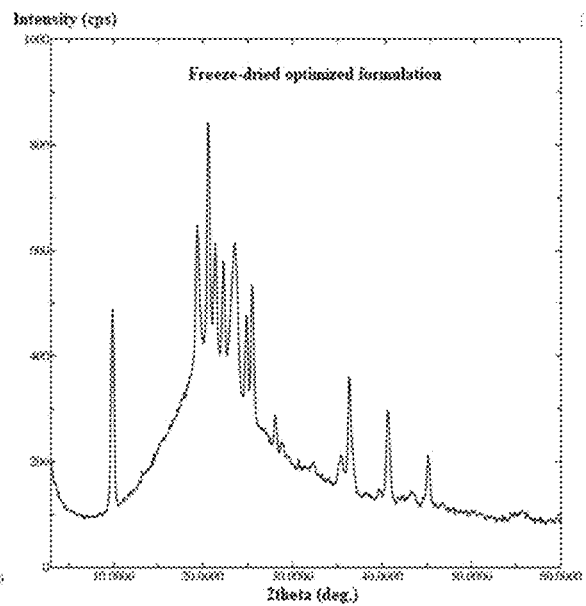
FIG. 9A  FIG. 9B
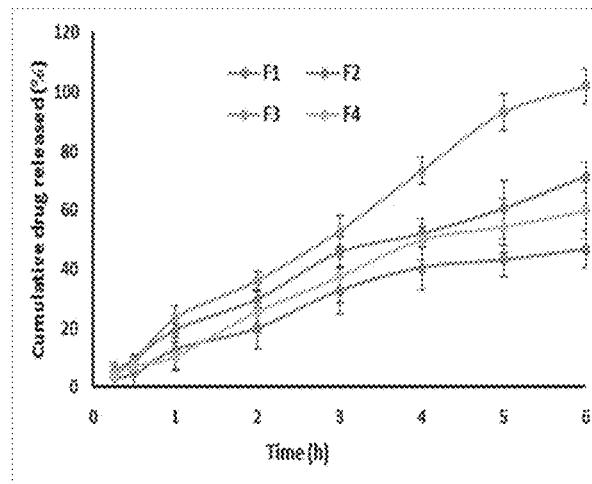 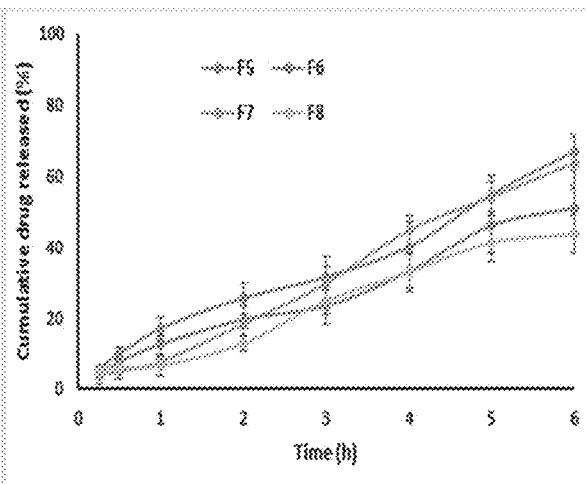
FIG. 10A  FIG. 10B

KETOCONAZOLE OPHTHALMIC PREPARATIONS CONTAINING TRANS-ETHOSOMAL DRUG NANOPARTICLES

FIELD OF THE INVENTION

The invention is generally related to ophthalmic ketoconazole formulations loaded with trans-ethosomal nanovesicles which are useful for the treatment of deep fungal eye infections. The disclosed formulations enhance the drug ocular permeation, antifungal activity, rapid drug drainage, and provide for a short elimination half-life.

BACKGROUND OF THE INVENTION

Various microorganisms such as bacteria, amoeba, viruses, and fungi can cause eye infections. Fungal infections are mostly developed as a result of an eye injury and can cause severe damage to the eye. People who have had corneal surgery are at higher risk of fungal eye infections. Many different types of fungi such as *fusarium, aspergillus, cryptococcus, histoplasma*, zygomycetes, and *candida* may cause ocular infection. These fungi are widely spread and can live in soil, plants, indoor, and outdoor environments or even on the human skin and body mucous membranes. They can affect and cause serious damage to many parts of the eye such as the eyelid (eyelid nodules), conjunctiva (conjunctivitis), cornea (keratitis), choroid (choroiditis), retina (retinitis), the inside vitreous and/or aqueous humor (endophthalmitis), and the optic nerve (optic neuropathy) (1). Mycotic keratitis and endophthalmitis are the major fungal prone infections. Mycotic keratitis usually occurs along with trauma to the cornea with the substance of plant origin. Keratitis, which is caused by fungi such as *candida*, typically occurs in patients with eye defects such as dry eye, chronic corneal ulceration, or corneal scarring. Endophthalmitis may be exogenous and endogenous. The former implies that blood-borne microbial infection has occurred as a result of metastatic spread of infection from other sites such as infected heart valves or the urinary tract. On the other hand, exogenous endophthalmitis results from a post-operative complication of lens removal, prosthetic lens implantation, or corneal transplantation (2-4).

Ketoconazole (KET) is a synthetic derivative of phenylpiperazine. It possesses a broad-spectrum antifungal activity and inhibits the synthesis of the fungal ergosterol by suppressing activity of the cytochrome P450 14α-demethylase. KET belongs to the Class II biopharmaceutical classification system, i.e., it is characterized by low aqueous solubility or high lipid solubility (log P=4.74) and high permeability (5). It undergoes extensive hepatic metabolism by oxidative O-dealkylation and by aromatic hydroxylation. The United States Food and Drug Administration has indicated that oral KET pharmacotherapy may cause severe liver damage, adrenal gland problems, and many other side effects (6). KET is a lipophilic broad spectrum antifungal agent that has a high molecular weight of 531.44 Da. Accordingly, these characters hinder drug transport across the corneal stroma during treatment of ophthalmic fungal infections, especially those that affect the posterior segment. Different formulation approaches have been developed to minimize KET side effects, enhance drug therapeutic activity, and sustain drug delivery. KET-loaded nanostructured lipid carrier, nano-sponges, poly(lactide-co-glycolide) nanoparticles, and lipid-polyethylene glycol-based nanoparticles have recently been reported to achieve effective treatment of fungal keratitis (7-10).

The term "trans-ethosomes" has been recently assigned for lipid-based nanovesicles that contain ethanol and an edge activator. Trans-ethosomes combine the advantages of ethosomes and transfersomes. The presence of these components makes trans-ethosomes possess superior advantages in drug delivery when compared with other delivery systems. Ethanol increases the fluidity of lipids and decreases the density of the lipid bilayer; as such, it enhances drug penetration through the tiny openings formed in the stratum corneum due to fluidization (11). The presence of the edge activator in these vesicles weakens the phospholipid bilayer and makes the vesicle ultradeformable and highly elastic (12). Accordingly, a positive impact on the therapeutic activity is expected from these drug-loaded nanovesicles. However, no drug-loaded trans-ethosomes nanovesicles have been investigated for their application in ocular drug delivery.

New formulations that enhance the therapeutic activity and sustain delivery of KET are needed.

SUMMARY

Embodiments of the disclosure provide KET trans-ethosomes nanovesicles loaded into various ophthalmic in situ gel (ISG) and hydrogel preparations to enhance KET antifungal activity and minimize the drug's side effects usually encountered during its oral treatment. The formulations also provide for decreased eye irritation and improved ocular transport.

An aspect of the disclosure provides an ophthalmic formulation comprising transethosomes, wherein the transethosomes comprise a phospholipid, an edge activator, ethanol, and ketoconazole, wherein a surface of the transethosome is modified with a cationic charge inducing agent. In some embodiments, the phospholipid is L-α-phosphatidylcholine and the edge activator is polysorbate-80. In some embodiments, the cationic charge inducing agent is stearyl amine. In some embodiments, the stearyl amine is present in an amount of 10-20% w/w. In some embodiments, the edge activator is present in an amount of 10-25% w/w. In some embodiments, the ethanol is present in a hydration medium in an amount of 12-50% v/v. In some embodiments, a ketoconazole to phospholipid molar ratio is from 1:2 to 1:4. In some embodiments, the ketoconazole is present in an amount of 0.05-0.2% w/v. In some embodiments, the transethosomes have an average diameter of 130-170 nm. In some embodiments, the transethosomes have a zeta potential value of +30-40 mV.

Another aspect of the disclosure provides an in situ gelling composition comprising an ophthalmic formulation as described herein and a gelling agent. In some embodiments, the gelling agent is selected from the group consisting of sodium alginate, poloxamer 407, and prop-2-enoic acid. In some embodiments, the gelling agent is prop-2-enoic acid and wherein the gelling agent is present in an amount of 0.05-1.5% w/v. In some embodiments, the composition further comprises hydroxypropyl methylcellulose (HPMC). In some embodiments, the HPMC is present in an amount of 0.2-0.8% w/v.

Another aspect of the disclosure provides a hydrogel composition comprising an ophthalmic formulation as described herein and HPMC. In some embodiments, the HPMC is present in an amount of 1.5-2.5% w/v.

Another aspect of the disclosure provides a method for the sustained delivery of ketoconazole to a subject in need thereof, comprising ocularly administering a therapeutically effective amount of an ophthalmic formulation as described herein, an in situ gelling composition as described herein, or a hydrogel composition as described herein to the subject. In some embodiments, the subject has a fungal eye infection in a posterior eye segment.

BRIEF DESCRIPTION OF THE DRAWINGS

FIGS. 7A-D. Differential scanning calorimetry thermograms of (A) ketoconazole, (B) phospholipid, (C) stearyl amine, and (D) the freeze-dried optimized formulation.

FIGS. 9A-B. X-ray diffraction patterns of (A) pure ketoconazole and (B) the optimized freeze-dried trans-ethosomes formulation.

FIGS. 10A-B. In vitro ketoconazole release from the prepared ophthalmic formulations (A) F1-F4 and (B) F5-F8.

DETAILED DESCRIPTION

Figure 1A:
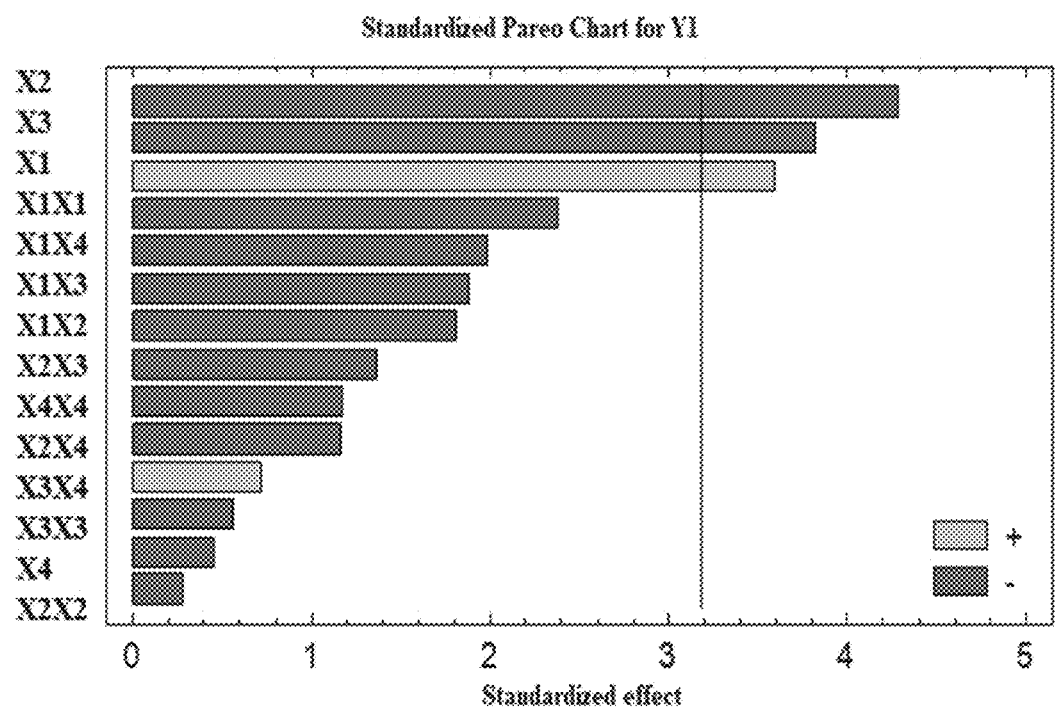
FIGS. 1A-D. Standardized Pareto charts for the effect of the studied factors on (A) $Y_1$, (B) $Y_2$, (C) $Y_3$, and (D) $Y_4$.
Figure 1B:
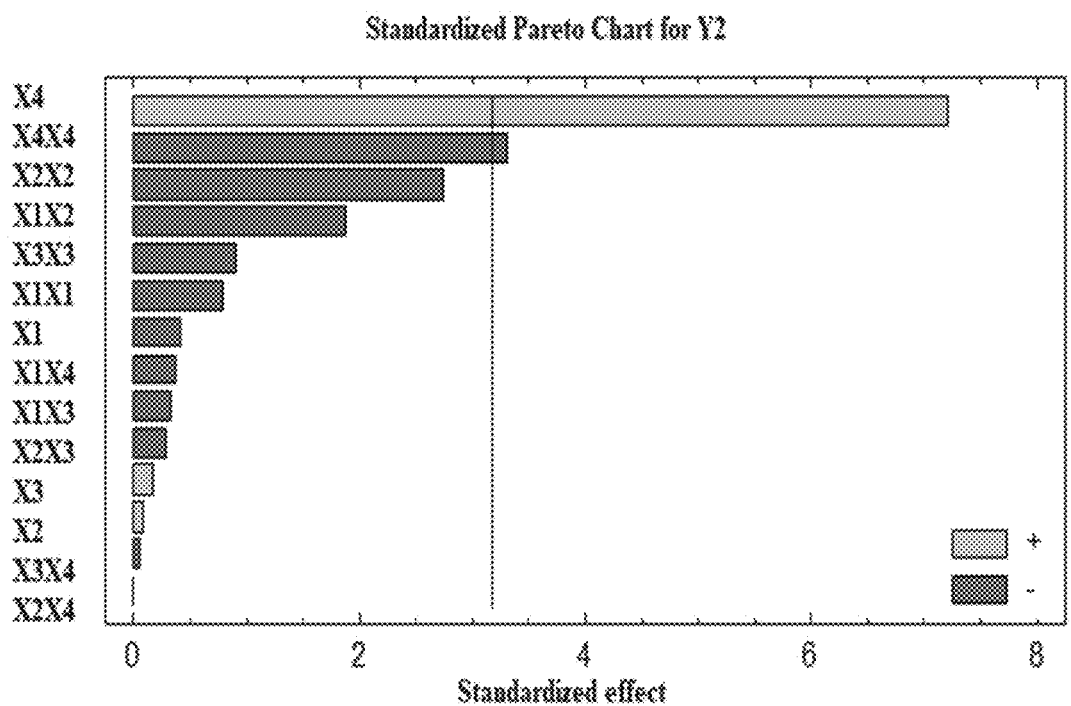
Figure 1C:
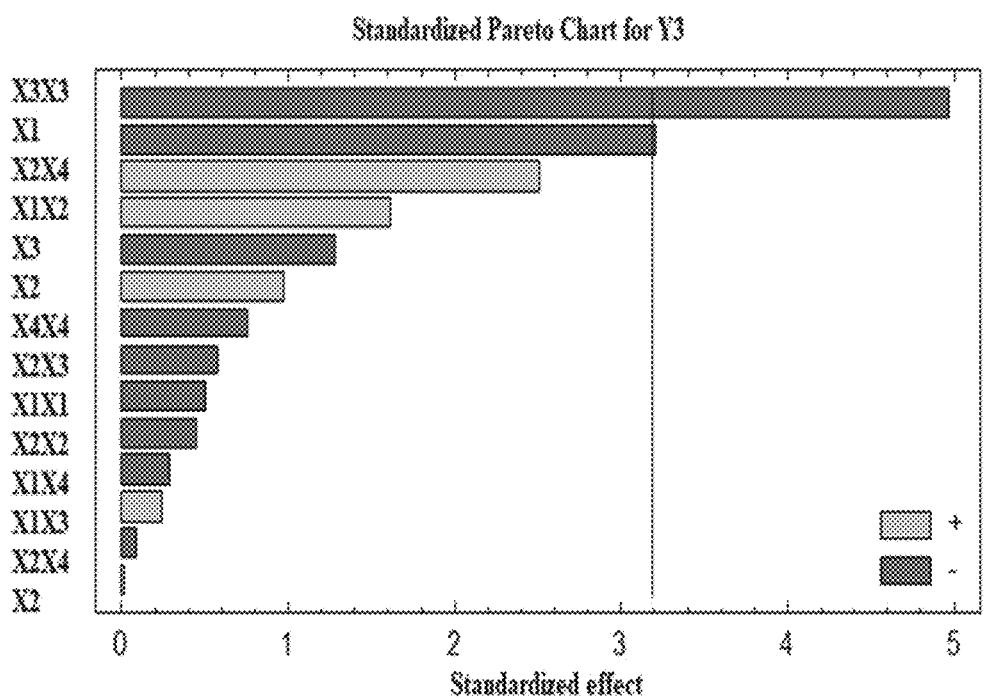
Figure 1D:
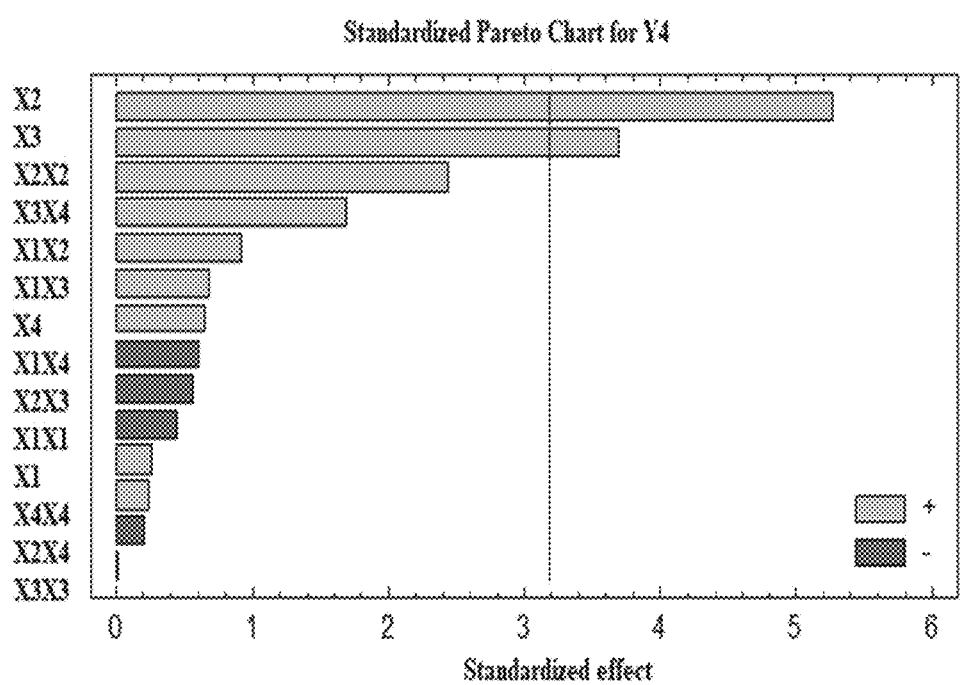
Figure 2A:
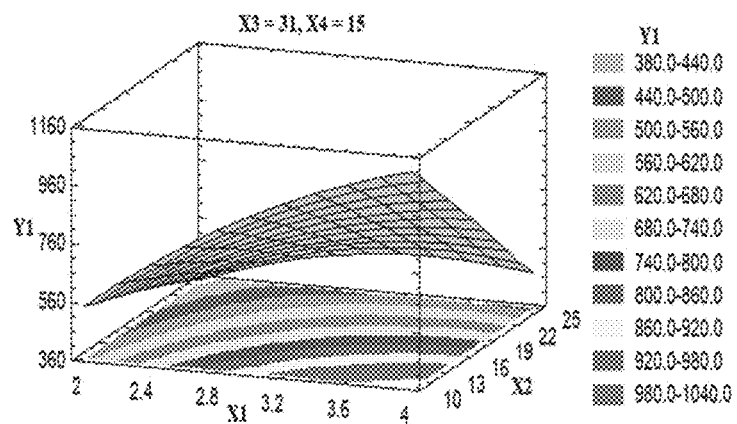
FIGS. 2A-F. Estimated response surface plots for the effect of the studied factors on the particle size ($Y_1$).
Figure 2B:
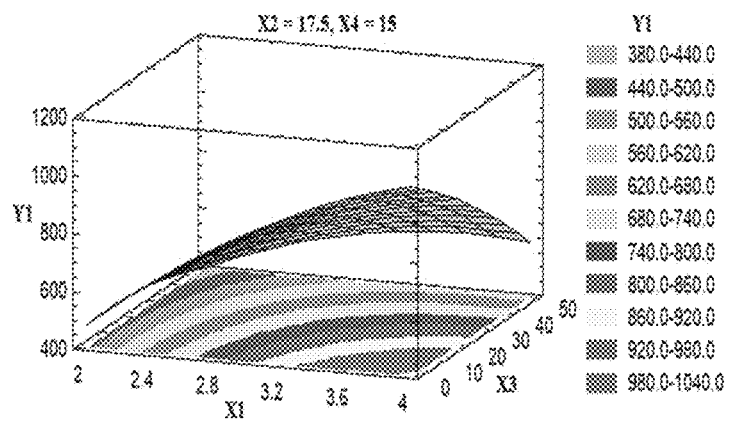
Figure 2C:
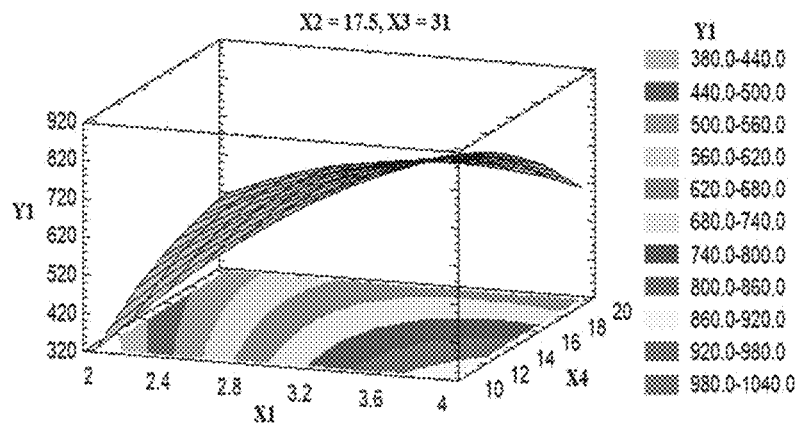
Figure 2D:
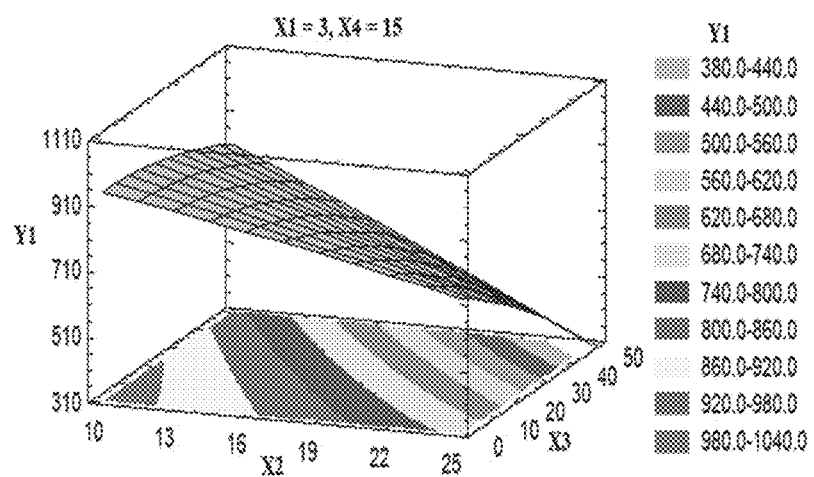
Figure 2E:
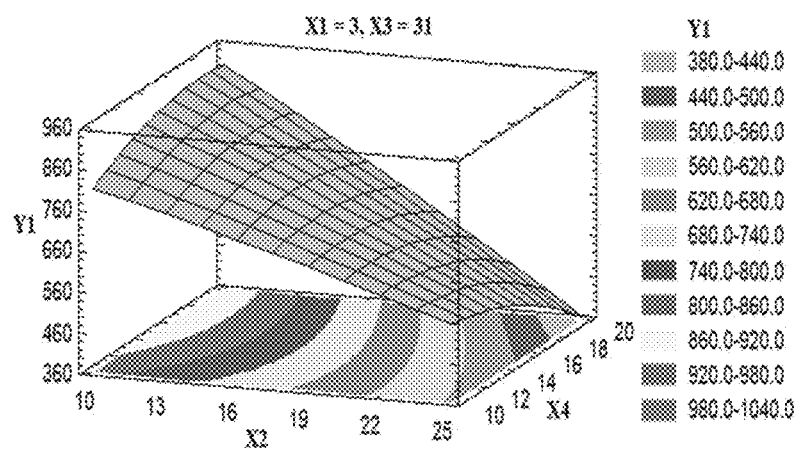
Figure 2F:
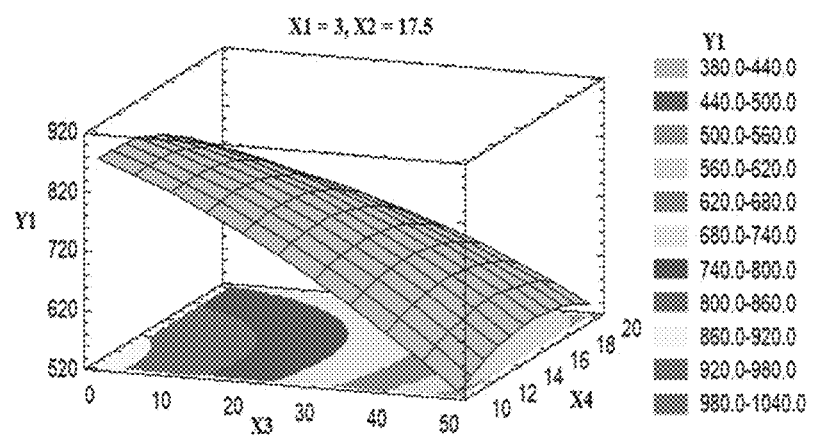
Figure 3A:
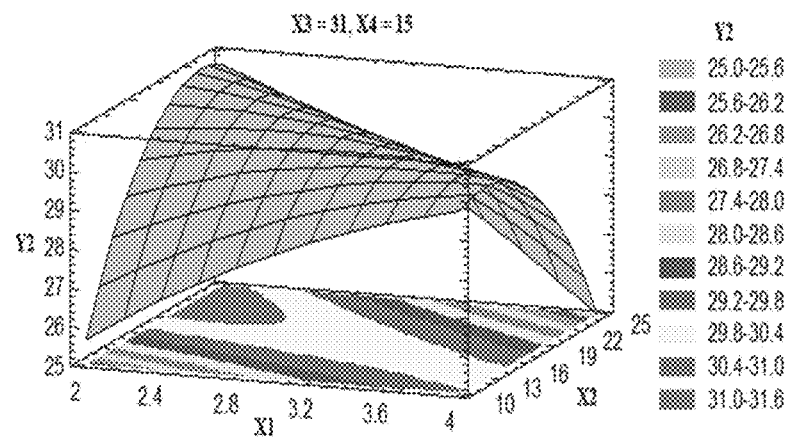
FIGS. 3A-F. Estimated response surface plots for the effect of the studied factors on the zeta potential ($Y_2$).
Figure 3B:
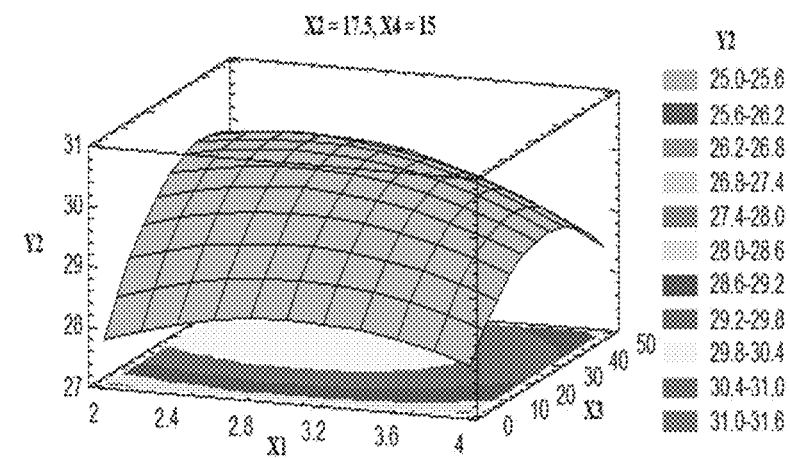
Figure 3C:
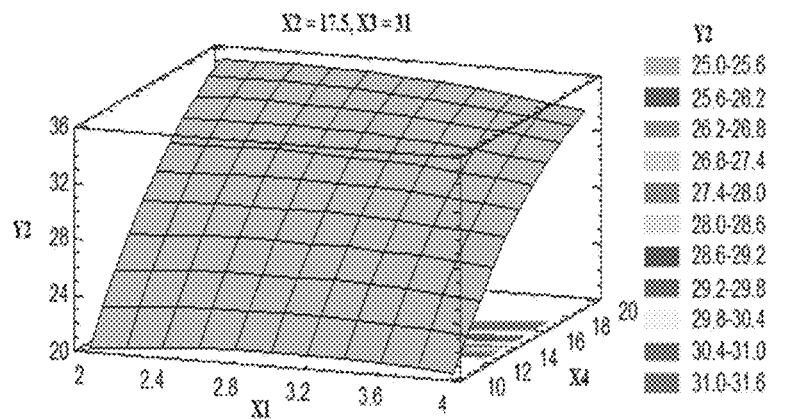
Figure 3D:
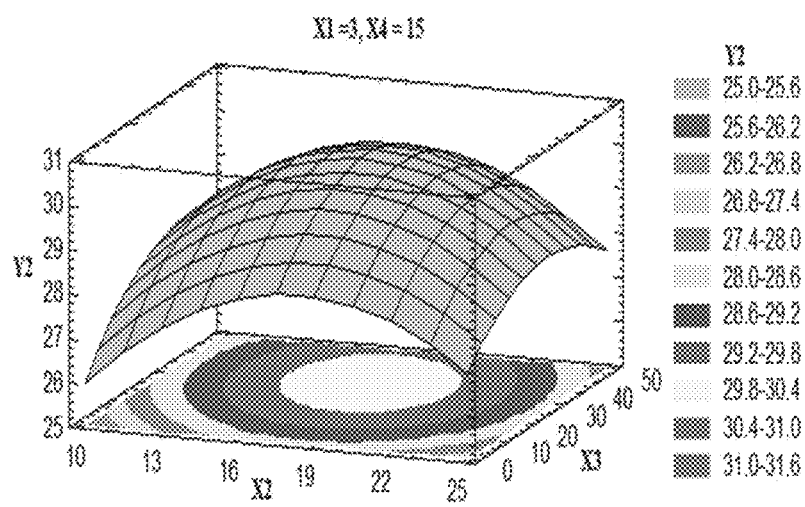
Figure 3E:
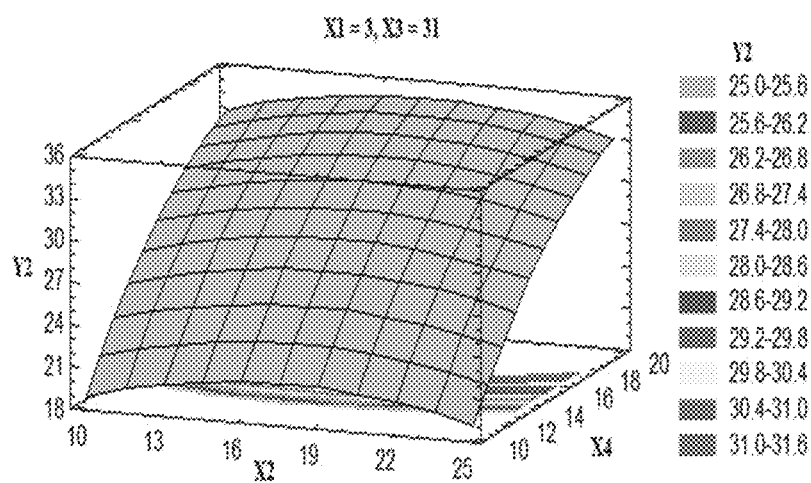
Figure 3F:
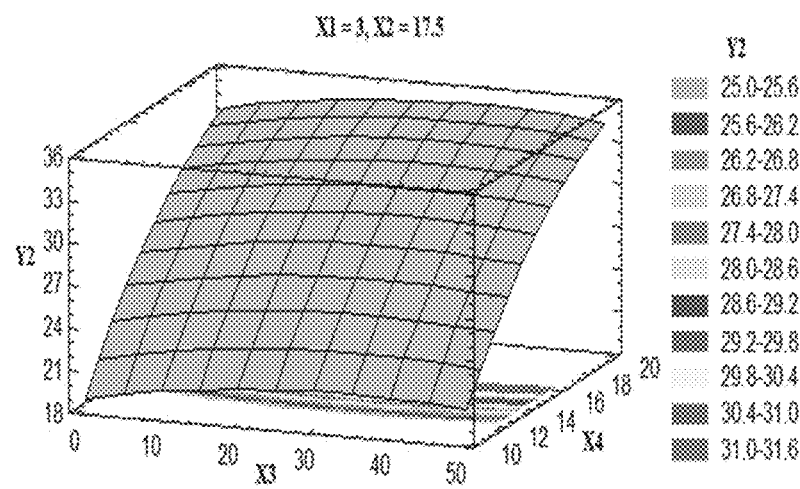
Figure 4A:
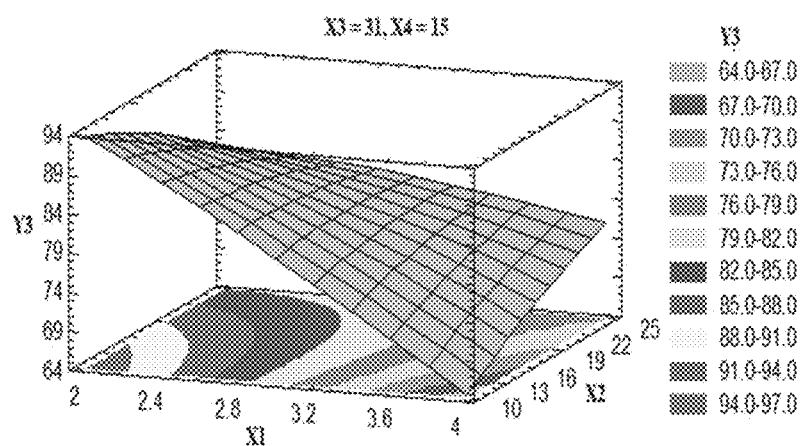
FIGS. 4A-F. Estimated response surface plots for the effect of the studied factors on the entrapment efficiency ($Y_3$).
Figure 4B:
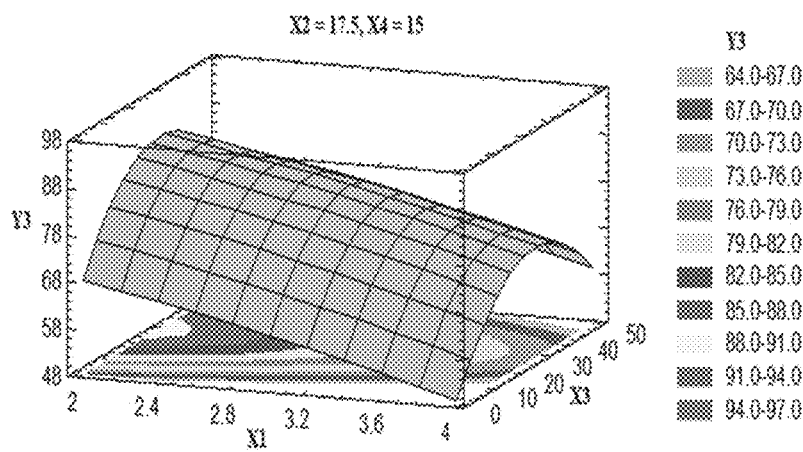
Figure 4C:
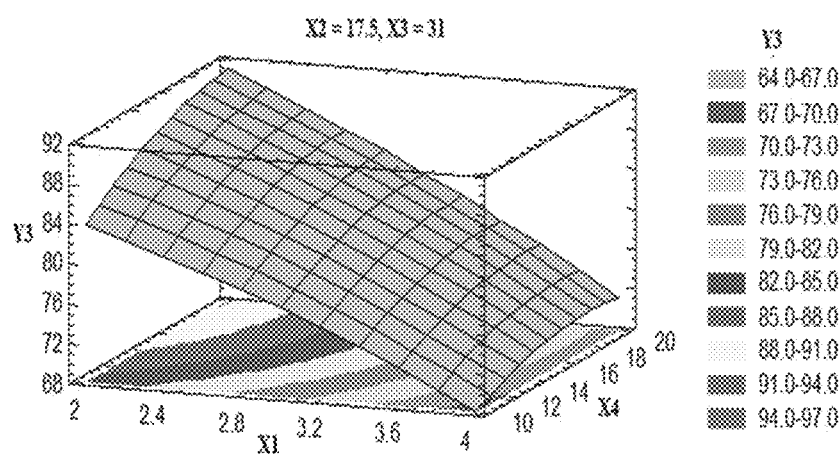
Figure 4D:
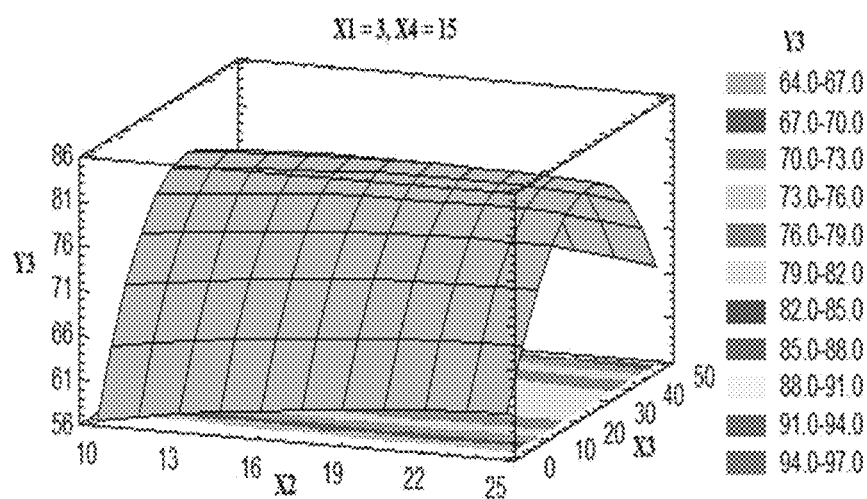
Figure 4E:
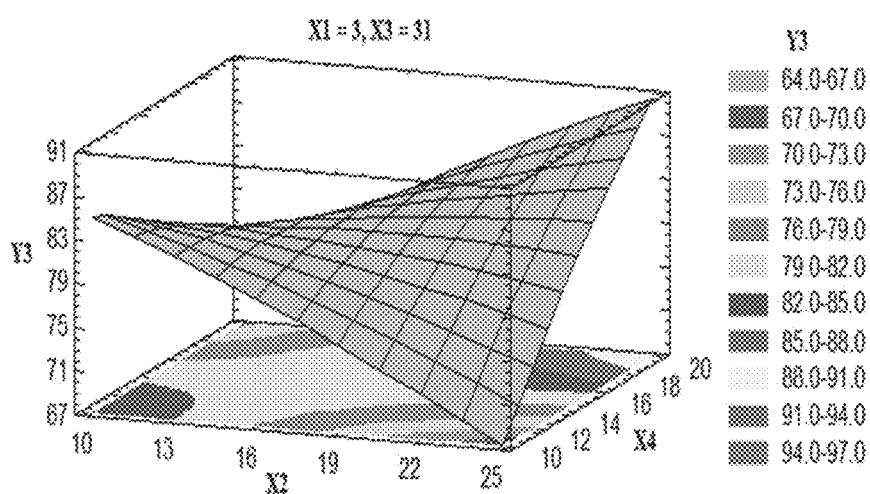
Figure 4F:
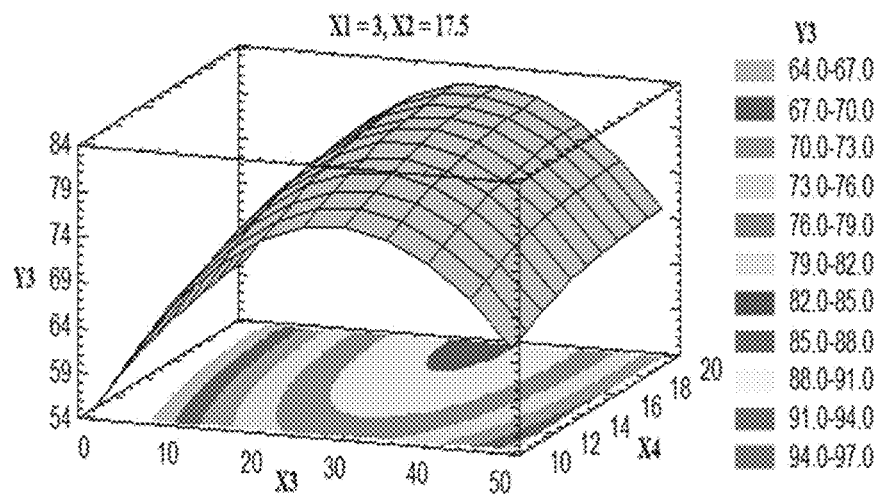
Figure 5A:
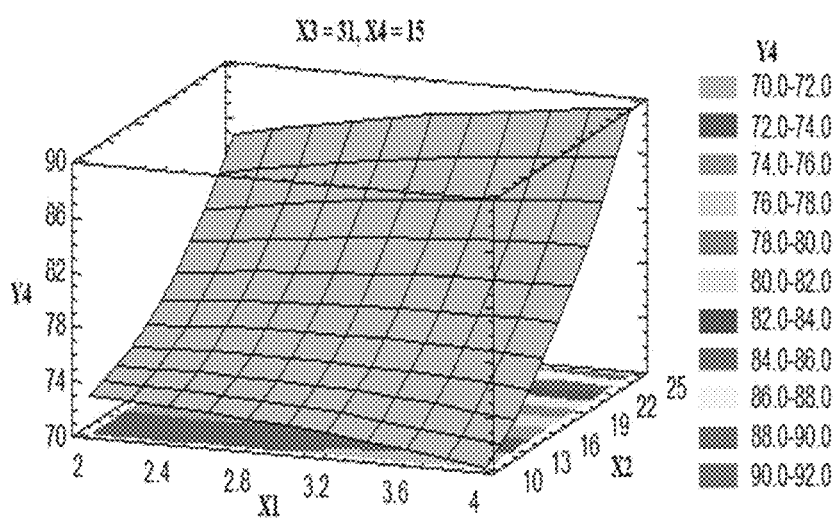
FIGS. 5A-F. Estimated response surface plots for the effect of the studied factors on the flexibility ($Y_4$).
Figure 5B:
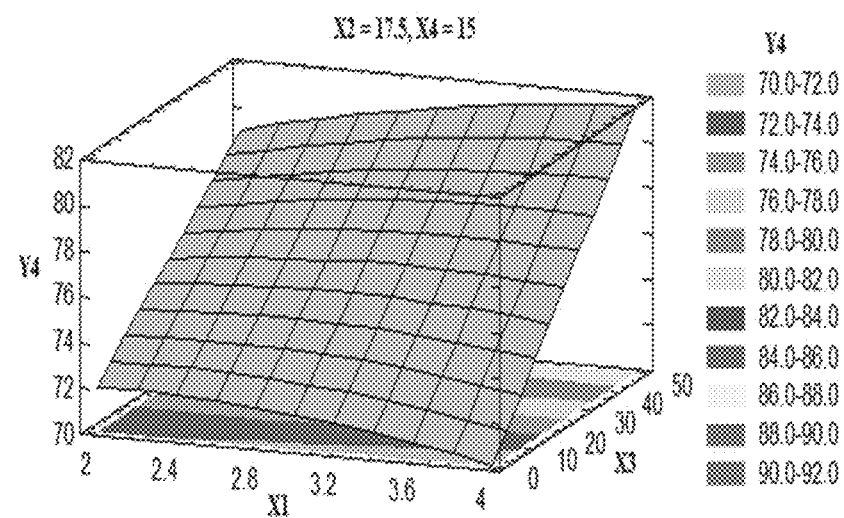
Figure 5C:
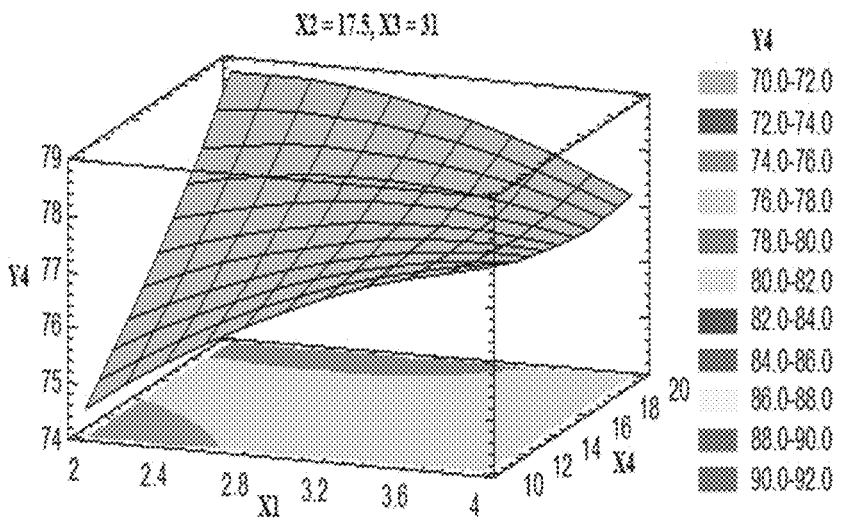
Figure 5D:
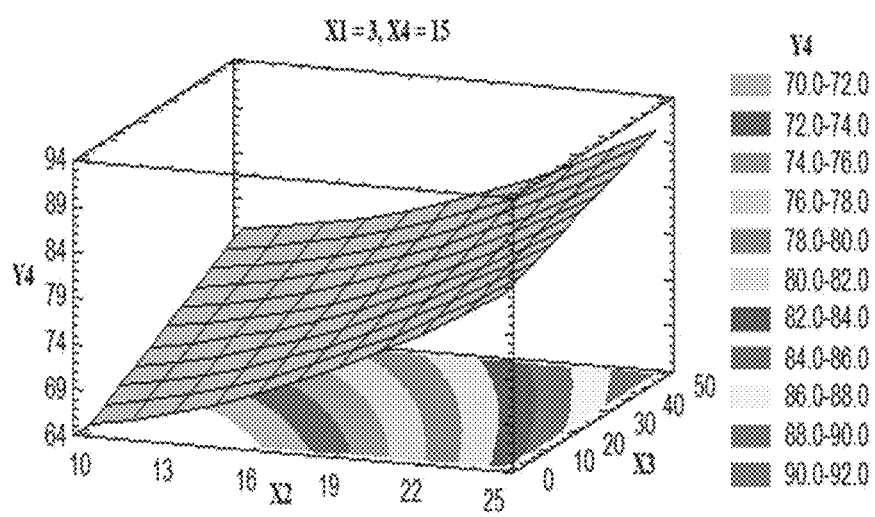
Figure 5E:
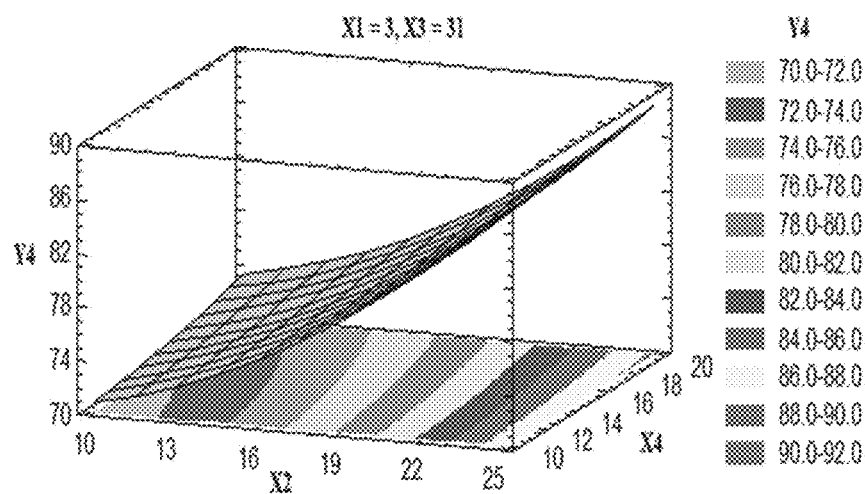
Figure 5F:
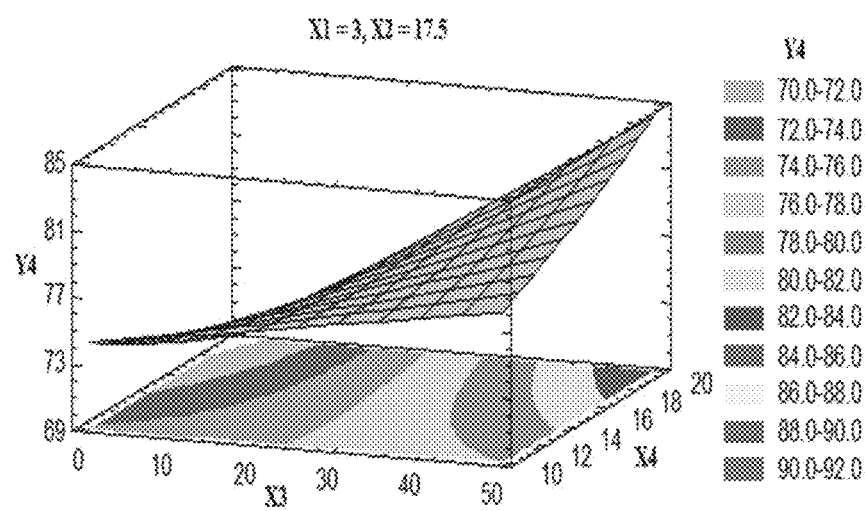

Embodiments of the disclosure provide ophthalmic formulations for the sustained delivery of ketoconazole, wherein the ketoconazole is incorporated into positively-charged transethosomes.

Transethosomes are flexible, lipid-based nanovesicles that are a combination of transferosomes and ethosomes. They contain phospholipid, edge activator, and ethanol. Transethosomes have previously been investigated for use in transdermal applications. These vesicular carrier systems have at least one inner aqueous compartment that is enclosed by a lipid bilayer, together with an edge activator/surfactant and ethanol. These vesicles may be used as vehicles for transporting active agents into the body, either by placing the active agent to be transported inside the lumen of the vesicle or incorporating the active agent into the membrane of the vesicle, as one of the membrane components. In some embodiments, the transethosomes have an average diameter of 130-170 nm, e.g. about 140-160 nm.

Phospholipids that may be incorporated in the transethosome include, but are not limited to, L-α-phosphatidylcholine, dilauroyl L-α-phosphatidylcholine, phosphatidylcholine stabilized with ascorbyl palmitate (i.e. Phospholipon 90 G), soy or egg phosphatidylcholine, dipalmitoylphosphatidylcholine, phosphatidylethanolamine (PE), phosphatidylserine (PS), pho sphatidic acid (PA), phosphatidylinositol (PI), phosphatidylglycerol (PG) and cardiolipin (CL).

In some embodiments, the formulation includes a ketoconazole to phospholipid molar ratio from 1:1 to 1:5, e.g. from 1:2 to 1:4. The at least one phospholipid is generally present in an amount ranging from about 0.1 to about 5.0% (w/v) of the total formulation volume, such as from about 0.5 to about 4.0% w/v or about 1 to about 3.5% w/v.

Edge activators function as membrane-destabilizing factors to increase the deformability of vesicle membranes and, when combined in a proper ratio with an appropriate lipid, gives the optimal mixture, enabling the transethosomes to become deformable, as well as ultra-flexible, which results in a higher permeation capability. Edge activators are amphiphilic molecules that contain a lipophilic alkyl chain that is connected to a hydrophilic head group. The edge activator may be selected from cationic surfactants, anionic surfactants, or nonionic surfactants with an uncharged polar head group. Nonionic surfactants are considered less toxic and less hemolytic, as well as less irritating to cellular surfaces, and they tend to maintain a near physiological pH in a solution. various nonionic surfactants and emulsifiers such as polysorbates, e.g. polyethylene sorbitol ester (polysorbate-type) nonionic surfactants such as polysorbate-20, polysorbate-40, polysorbate-60, and polysorbate-80. Commercially available polysorbates include the "Tweens", condensates of sorbitol fatty acid ester and ethylene oxide, common commercial brand names of which include Scattics, ALKEST® TW 20, and TWEEN 20®. In some aspects, the edge activator is polysorbate-80, the generic name for which is polyoxyethylene (20) sorbitan monooleate, and which is commercially available as TWEEN 80®. Other polysorbates are generally commercially available under similar naming conventions, e.g. TWEEN 20®, TWEEN 40®, TWEEN 60®, etc. Additional edge activators include the "Spans", such as SPAN 60®, SPAN 65®, SPAN 80®, etc., sodium cholate, sodium deoxycholate, and dipotassium glycyrrhizinate. In some embodiments, the edge activator is present in an amount of 5-30% w/w, e.g. 10-25% w/w.

The hydrophilic-lipophilic balance (HLB) of a surfactant is measured on an empirical scale developed by Griffin (W. C. Griffin, J. Cosmet. Chem., 1, 311, 1949). This scale ranges from 0 to 20, with 0 for a completely lipophilic molecule and 20 for a completely hydrophilic molecule. In some embodiments, the surfactant has a HLB value of about 10-17, e.g. about 12-15.

The presence of ethanol in the lipid layer of the transethosome provides a softer and malleable vesicle structure, which gives more freedom, elasticity and stability to its membrane. In some embodiments, the ethanol is present in a hydration medium, e.g. water or a buffer solution such as a phosphate buffer solution, in an amount of 5-60% v/v. e.g. 12-50% v/v.

The transethosomes may contain may contain one or more additional components such as a permeation enhancer (e.g. glyclols such as propylene glycol, C3-C4 alcohols, etc.).

In one embodiment, a surface of the transethosome is modified with a cationic charge inducing agent such as stearylamine, 1-alanine benzyl ester, or cetyltrimethylammonium bromide. The presence of positive charges on the vesicle surface allows for interaction with the negatively charged cell membrane, which enhances the penetration and effect. In some embodiments, the stearyl amine is present in an amount of 10-20% w/w of the total lipid. The zeta potential value, which indicates surface charge of the particles, generally ranges from +30-40 mV, e.g. about +33-37 mV.

The entrapment efficiency (EE) of the transethosomes generally ranges from about 80 to 100%, e.g. is at least about 80, 85, 90, 95 or 100%. In some aspects, the EE ranges from about 90-100%.

The flexibility value of the transethosomes generally ranges from about 90 to 100%, e.g. is about 91, 92, 93, 94, 95, 96, 97, 98, or 99%. Flexibility of the nanoparticles refers to the change in the nanoparticle size after extrusion under reduced pressure across a membrane filter of a specific pore size.

The transethosomes described herein are useful for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is ketoconazole. In some embodiments, the ketoconazole is present in an amount of 0.05-0.2% w/v of the total formulation volume.

In some embodiments, the transethosomes described herein are incorporated into in situ gelling (ISG) compositions. The ISG preparation may provide an extended drug residence time, accurate dosing, and extended shelf-life. Conventional ophthalmic preparations may be rapidly eliminated from the eyes due to the reflex high tear fluid turnover and eye dynamic Polymers such as gellan gum, alginic acid, Carbopol® (carbomer), and poloxamer can be utilized to develop aqueous solutions that undergo gelation when instilled into the eye. This effect results in a prolongation of drug contact time, a decrease in the frequency of dosing, and an increase in the transcorneal penetration. Ophthalmic ISG formulations are administered as a liquid and congeal in the cul-de-sac in response to physiological conditions. This behavior results in higher drug bioavailability and slower rate of drainage at the corneal site. Sol-to-gel transformation can be triggered by changes in temperature, pH, ion activation, osmolality, and/or water concentration. For example, if poloxamer is used, the transformation may be triggered by increasing the temperature to at least about 34° C. If carbomer is used, the transformation may be triggered by raising the pH to at least 7.4. If sodium alginate is used, the transformation may be triggered by adding at least 0.5 M CaOH. In some embodiments, the gelling agent is a cross-linked polyacrylic acid polymer such as prop-2-enoic acid (i.e. Carbopol® 940). In some embodiments, the gelling agent is present in an amount of 0.05-1.5% w/v of the total formulation.

Additional components such as a viscosity modifier, e.g. hydroxypropyl methylcellulose (HPMC), may be added to the ISG composition. In some embodiments, the HPMC is present in an amount of 0.2-0.8% w/v of the total formulation.

The in situ gelling composition as described herein may be reconstituted in water. Aqueous suspensions containing the composition may have one or more excipients suitable as suspending agents, for example pharmaceutically acceptable synthetic gums such as HPMC or natural gums. Oily suspensions may be formulated by suspending the composition in a vegetable oil or mineral oil. The oily suspensions may contain a thickening agent such as beeswax or cetyl alcohol.

Further embodiments of the disclosure provide a hydrogel composition comprising an ophthalmic formulation as described herein and a hydrophilic polymer such as HPMC. A hydrogel comprises a crosslinked hydrophilic polymer that does not dissolve in water. In some embodiments, the polymer is present in an amount of 1.5-2.5% w/v of the total formulation.

The formulations/compositions described herein provide for the sustained release of an active agent to the eye. As used herein, the phrase "sustained release" generally refers to the release of the active agent over an extended period of time leading to relatively lower peak plasma concentrations and a prolonged bioavailability as compared to "immediate release" formulations of the same active ingredient. More precisely, the phrase "sustained release" refers to the release of the drug from the pharmaceutical composition over a period substantially longer than 6 hours, such as about 7, 8, 9, or 10 hours or longer. Generally, the sustained release of drug occurs at such a rate that blood (for example, plasma) concentration in a patient to whom the pharmaceutical composition is administered exhibits reduced levels when compared to blood concentration in a patient to whom an immediate-release formulation is administered. In some embodiments, the composition has an entire release of about 40-80% after 6 hours, e.g. about 40-50%.

The formulations/compositions described herein may contain one or more pharmaceutically acceptable ingredients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example an inert diluent such as lactose; granulating and disintegrating agents such as cornstarch; binding agents such as starch; and lubricating agents such as magnesium stearate.

The compositions of the present disclosure may also contain other components such as, but not limited to, antioxidants, additives, adjuvants, buffers, tonicity agents, bioadhesive polymers, and preservatives. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure include methods of preparing transethosomes, in situ gelling compositions, and hydrogel compositions as described herein.

Transethosomes may be prepared according to a thin film hydration method in which the drug, phospholipid, and edge activator are dissoved in a solvent such as methanol. The mixture may be subject to homogenization, e.g. using a water bath sonicator, to obtain a homogenous dispersion. The solvent is removed under reduced pressure until a thin clear lipid film is formed. The dried lipid film may then be hydrated in a hydration medium such as phosphate buffer containing ethanol and propylene glycol. The prepared transethosomes formulations may then be subjected to probe sonication to achieve particle size reduction.

ISG formulations may be prepared by simple dispersion of the gelling agent in a known volume of the drug loaded transethosomes formulation over a magnetic stirrer.

Hydrogels may also be prepared by dispertion by adding the polymer to a known volume of the drug loaded transethosomes formulation over a magnetic stirrer.

The present disclosure also provides a method for the sustained-delivery of an active agent to a human or non-human animal subject in need thereof by ocularly administering to said subject a transethosome composition, in situ gelling composition, or hydrogel composition as described herein.

The compositions of the disclosure may be useful for the treatment of any disease or disorder that the included active agent is useful for treating. For example, if ketoconazole is used, the composition or dosage form may be useful for the treatment of fungal or yeast infections. In particular, the compositions are useful for treatment of deep fungal infections in the posterior segment of the eye. The posterior segment of the eye comprises the back two-thirds of the eye, including the vitreous humor, the retina, the choroid and the optic nerve. The compositions are also useful stabilizers for active agent storage.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. ketoconazole) is administered to the subject in a therapeutically effective amount. By a "therapeutically effective amount" is meant a sufficient amount of active agent to treat the infection, disease, or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4 or more times weekly.

Whilst the beneficial effects of the disclosure are particularly apparent in ocular delivery, e.g. as an eye drop, the utility of the disclosure is not limited and compositions according to the invention may also used for oral, transdermal, intranasal, buccal, rectal, vaginal, ocular, intraperitoneal, and parenteral drug delivery.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Ketoconazole (KET), a synthetic imidazole broad-spectrum antifungal agent, is characterized by its poor aqueous solubility and high molecular weight, which might hamper its corneal permeation. The aim was to develop an ophthalmic formulation loaded with optimized trans-ethosomal vesicles to enhance KET ocular permeation, antifungal activity, rapid drug drainage, and short elimination half-life. Four formulation factors affecting the vesicles' size, zeta potential, entrapment efficiency, and flexibility of the trans-ethosomes formulations were optimized. Different ophthalmic formulations loaded with the optimized vesicles were prepared and characterized. The ocular irritation and in vivo corneal permeation were investigated. Results revealed that the drug-to-phospholipid-molar ratio, the percentage of edge activator, the percentage of ethanol, and the percentage of stearyl amine significantly affect the characteristics of the vesicles. The optimized vesicles were spherical and showed an average size of 151.34±8.73 nm, a zeta potential value of +34.82±2.64 mV, an entrapment efficiency of 94.97±5.41%, and a flexibility of 95.44±4.33%. The antifungal activity of KET was significantly improved following treatment with the optimized vesicles. The developed in situ gel formulations were found to be nonirritating to the cornea. The trans-ethosomes vesicles were able to penetrate deeper into the posterior eye segment without any toxic effects. Accordingly, the developed in situ gel formulation loaded with KET trans-ethosomes vesicles represents a promising ocular delivery system for treatment of deep fungal eye infections.

Materials and Methods

Materials

Ketoconazole was a kind gift from Saudi Arabian Japanese Pharmaceuticals Company (Jeddah, Kingdom of Saudi Arabia). L-α phosphatidylcholine (95%) (soy), average molecular weight of 775.037 was procured from Avanti® polar lipids, INC. (Alabaster, Ala., USA). Tween® 80 (polyoxyethylene sorbitan monooleate) methanol, ethanol, propylene glycol (PG), stearyl amine and fluorescein isothiocyanate (FITC)-dextran were procured from Sigma-Aldrich (St. Louis, Mo., USA). Poloxamer 407 was obtained from Xi'an Lyphar Biotech Co., LTD (Xi'an, China). Sodium alginate was purchased from VWR International Co., Ltd. (Poole, England). Carbopol 940 and hydroxypropyl methylcellulose (HPMC) Mwt 86,000 g/mol, viscosity 4000 cp (2% solution) were obtained from Acros Organics (Morris Plains, N.J., USA). All other chemicals and solvents were of analytical grade.

Development of KET Trans-Ethosomes Vesicles

Draper-Lin Small Composite Experimental Design

Response surface methodology is a statistical tool used to explore the effect of several formulation and/or processing factors on one or more response variables. The proper design is selected to optimize the process or the formulation. In this work, four formulation factors that affect the vesicle size ($Y_1$), zeta potential value ($Y_2$), the entrapment efficiency ($Y_3$), and the flexibility ($Y_4$) of KET-loaded trans-ethosomes were studied using the Draper-Lin small composite experimental design utilizing the StatGraphics Centurion XV version 15.2.05 software, StatPoint Technologies, Inc. (Warrenton, Va., USA). The design space included the effect of four variables i.e., the drug-to-phospholipid molar ratio ($X_1$), the percentage of edge activator of the total lipid ($X_2$), the percentage of ethanol in the hydration medium ($X_3$), and the percentage of stearyl amine of the total lipid ($X_4$). Table 1 represents the levels of the studied factors and the desired goal for the studied responses used in the Draper-Lin small composite design. Eighteen runs were suggested, and the composition of these trans-ethosomal nanoparticles formulations is disclosed in Table 2.

TABLE 1

Ketoconazole trans-ethosomes dependent and independent variables used in the Draper-Lin small composite experimental design.

| | Level | |
|---|---|---|
| Independent Variables | Low | High |
| $X_1$; Drug: phospholipid molar ratio | 1:2 | 1:4 |
| $X_2$; % (w/w) of edge activator of the total lipid | 10 | 25 |
| $X_3$; % (v/v) of ethanol in the hydration medium | 12 | 50 |
| $X_4$; % (w/w) of stearyl amine of the total lipid | 10 | 20 |
| Dependent Variables | Goal | |
| $Y_1$; Vesicle size (nm) | Minimize | |
| $Y_2$; Zeta potential (mV) | Maximize | |
| $Y_3$; Entrapment efficiency (%) | Maximize | |
| $Y_4$; Flexibility (%) | Maximize | |

Preparations of KET trans-ethosomes

KET trans-ethosomes were prepared according to the thin film hydration method previously described (18-20), except for slight modification. Based on the formulation's composition illustrated in Table 2, the calculated amount of KET, L-α-phosphatidylcholine, tween 80, and stearyl amine was placed in a long-necked round-bottom flask and dissolved in a specified volume (50 mL) of methanol. A drug concentration of 0.1% w/v, based on the total trans-ethosomal formulation, was used. The mixture was subjected to homogenization using CF3 2EY water bath sonicator, Ultra-wave Ltd., (Cardiff, UK) until a homogenous dispersion was obtained. The organic solvent (methanol) was removed slowly under reduced pressure at 50° C. using Buchi Rotavapor R-200, Buchi labortechink AG, CH-9230 (Flawi, Switzerland) until a thin clear lipid film was formed on the flask wall. The flask was kept overnight in a vacuum oven, model 6505, of Thermo Fisher Scientific (Oakwood Village, Ohio, USA) to ensure complete removal of methanol. The dried lipid film was hydrated at 40° C. using 40 mL of phosphate buffer pH 7.4 containing the specified amount of ethanol and PG (1%). The later was added as an enhancer (21). The prepared trans-ethosomes formulations were subjected to probe sonication under ice, using Sonics Vibra cell, VCX 750; Sonics & Materials, Inc. (Newtown, CT, USA) for about 10 min at an amplitude of 60% to achieve particle size reduction.

Characterization of the Prepared Trans-Ethosomes Formulations

Particle Size, Polydispersity Index, and Zeta Potential Measurements

The average particle size, polydispersity index (PDI), and the zeta potential value for the 18 KET trans-ethosomes formulations were estimated using Malvern Zetasizer Nano ZSP, Malvern Panalytical Ltd. (Malvern, United Kingdom). The dynamic light-scattering technique with noninvasive backscatter optics and laser doppler micro-electrophoresis were utilized for measurement of particles size and zeta potential, respectively. All sample measurements were repeated in triplicate.

Entrapment Efficiency (EE)

The percentage of KET successfully entrapped in the trans-ethosomes formulations was estimated indirectly. Briefly, the prepared trans-ethosomes dispersions were subjected to centrifugation at 20,000 rpm for 60 min at 4° C. using 3 K30 Sigma Laboratory centrifuge (Ostrode, Germany). The supernatant containing the free drug was separated, filtered through an Acrodisc® syringe filter of 0.2 μm, and diluted with methanol. The concentration of free KET was analyzed spectrophotometrically at $\lambda_{max}$ of 240 nm. The percentage EE of KET was calculated using the following equation:

$$EE\ (\%) = \frac{\text{(Total amount of KET used} - \text{Calculated amount of free KET in the supernatant)}}{\text{(Total amount of KET used)}} \times 100 \quad (1)$$

Vesicles Flexibility

The extrusion method was used to determine the flexibility of the developed KET trans-ethosomes vesicles as previously reported (21,22), except for slight modification. The prepared vesicles were extruded through a nylon membrane filter of pore size 0.1 mm under reduced pressure of 2.5 bar using Charles Austin Dymax 14 air pump (Walton-on-the-Naze, United Kingdom). The percentage change in the size of the vesicles before and after extrusion was measured, and flexibility was calculated according to the following equation:

$$\text{Flexibility}(\%) = \left[\frac{\text{Vesicle size before extrusion} - \text{Vesicle size after extrusion}}{\text{Vesicle size before extrusion}}\right] \times 100 \quad (2)$$

Draper-Lin Small Composite Statistical Analysis

The data obtained for the studied responses ($Y_1$, $Y_2$, $Y_3$, and $Y_4$) were introduced into the response column of the StatGraphics software and statistically analyzed to identify the significant independent factors affecting each response. A P-value<0.05 was considered significant. The optimum desirability was identified, and the optimized formulation that achieve the study goal was proposed.

Development of the Optimized Trans-Ethosomes Formulation

An optimized KET trans-ethosomes formulation that contains 1.71, 28.69, 42.75, and 23.36 of $X_1$, $X_2$, $X_3$, and $X_4$, respectively, was prepared and characterized for particle size ($Y_1$), zeta potential ($Y_2$), entrapment efficiency ($Y_3$), and flexibility ($Y_4$), as previously mentioned.

Morphological Study of the Trans-Ethosomal Nanovesicles

Morphology of the optimized formulation was examined using transmission electron microscopy (TEM) model JEM-1230, JEOL (Tokyo, Japan). A few drops of the formulation were placed on a carbon-coated grid and left for about 5 min to allow better adsorption of the nanovesicles on the carbon film. Excess liquid was removed using filter paper. Finally, a few drops of phosphotungstic acid (1%) were added, and the sample was examined Solid-State Physicochemical Characterization Differential Scanning Calorimetry (DSC)

The thermal behavior of pure KET, the studied phospholipid, stearyl amine, and the freeze-dried KET trans-ethosomes formulation were investigated using a Shimadzu DSC-TA-50 ESI apparatus (Tokyo, Japan). A specified weight (2 mg) of each sample was placed in an aluminum crucible under an atmosphere of nitrogen. The prepared samples were heated at a rate of 10° C./min in the range of 25–300° C.

Fourier Transform Infrared Spectroscopy (FT-IR)

The FT-IR spectrum of pure KET, phospholipid, stearyl amine, and the prepared trans-ethosomes formulation was studied using a Nicolet Is10 FT-IR spectrometer of Thermo Scientific, Inc. (Waltham, Mass., USA). The spectra of the samples were recorded in the range of 4000-400 cm$^{-1}$.

X-Ray Powder Diffraction (XRPD)

To examine the change in the drug crystalline state after development of the trans-ethosomes nanovesicles, the diffraction pattern of pure KET and the freeze-dried KET trans-ethosomes formulation were analyzed using a D/max 2500; Rigaku, powder X-ray diffractometer (Tokyo, Japan). The diffraction pattern of the studied samples was recorded at a scan speed of 0.5° C./min.

Antifungal Activity of KET Trans-Ethosomes Nanovesicles

To study the antifungal activity of the optimized KET trans-ethosomes formulation, a standard strain of *Candida albicans* ATCC 76615 was used. The agar well diffusion technique was utilized in this experiment as previously reported (23). Briefly, petri dishes of 150 mm diameter were prepared by placing 50 mL of Müller-Hinton agar containing 1 mL fungal culture (1×10$^6$ CFU/mL) into each dish. The fungal strain was subsequently inoculated. Holes of 12 mm diameter were made and filled with 200 μL of the studied formulation. The prepared dishes were incubated for 4 h at 37° C. The area where there is an absence of any fungal growth around the holes (inhibition zone) was measured using a caliper. For comparative study, the antifungal activity of the trans-ethosomes nanovesicles was compared to a drug suspension (positive control) and plain trans-ethosomes formulation (negative control).

Development of Ophthalmic Preparations Loaded with KET Trans-Ethosomes

Preparation of In Situ Gel and Hydrogel Formulations

Different in situ gel (ISG) formulations were prepared by simple dispersion of the specified quantity of sodium alginate (1%), poloxamer 407 (16%), or carbopol 940 (1%) in a known volume of the optimized drug loaded trans-ethosomes formulation over a magnetic stirrer. Stirring was continued until complete dispersion of the polymer and formation of homogenous mixture without lumps or precipitate. HPMC (0.5% w/v) was added as a viscosity modifier. For comparative study, pure KET-loaded ISG formulations were prepared in deionized water. The prepared ISG formulations were stored at 4° C. until further characterization.

Ophthalmic HPMC hydrogels were also prepared by adding the specified weight of the polymer to a known volume of either the optimized KET trans-ethosomes nanovesicles or deionized water containing pure KET over a magnetic stirrer. Stirring was continued until complete dispersion of the polymer. The prepared hydrogels were stored at 4° C. until further characterization. A total of six ISG and two HPMC hydrogel formulations were prepared, and their composition is illustrated in Table 4.

Characterization of the Prepared Ophthalmic Formulations
Rheological Properties

The rheological behavior of the prepared ophthalmic formulations (0.5 g) was studied by means of a Brookfield DV III ultra V6.0 RV cone and plate rheometer (Middleboro, Mass., USA) using spindle #CPE40 at 25±3° C. Angular velocity was gradually increased from 0.5 to 100 rpm. Viscosity of the ISG formulations was measured (n=3) before and after gelation. Gelation of the poloxamer-based ISG formulations (F1 and F2) was induced by increasing the temperature to 34° C. For carbopol-based ISG formulations (F3 and F4), gelation was achieved by raising the pH to 7.4 by adding 0.5 M NaOH. Gelation of the alginate-based ISG formulations (F5 and F6) was done by adding 0.5 M CaOH.

In Vitro Release Study

The in vitro release of KET from the prepared ISG and hydrogel formulations was evaluated using the dialysis bag method, as previously reported (24). Known quantity of each formulation (equivalent to 9 mg drug) was placed in a firmly sealed dialysis bag of Sigma-Aldrich Inc. (molecular weight cut-off 14 k Da). A definite volume of simulated tear fluid (STF; 0.67% w/v sodium chloride; 0.2% w/v sodium bicarbonate; and 0.008% w/v calcium chloride in deionized water; and the pH was adjusted to 7.4 using hydrochloric acid) was added in a ratio of 25:7 (formulation: STF) to mimic the condition in the human eye. The dialysis bag was immersed in a glass bottle holding 250 mL of phosphate buffer pH 7.4. The prepared bottles were kept in a shaking water bath, Model 1031; GFL Corporation (Burgwedel, Germany) at 32° C. and 100 rpm. Aliquots of 3 mL were taken at predetermined time intervals with an immediate replacement to maintain sink condition. The concentration of KET in these samples was determined spectrophotometrically at 240 nm against a blank of nonmedicated carbopol-based ISG formulation (control formulation). The experiment was done in triplicate.

To investigate KET release kinetics and the drug release mechanism from the prepared formulations, the obtained results for the in vitro release were fitted to different mathematical models, namely, zero (25), first (25), Higuchi (26), and Korsmeyer-Peppas (27,28). In vivo ocular irritation test The therapeutic dose of KET in dogs is 10-40 mg/kg/day, while rats may be dosed up to 100 mg/kg/day (29). Since our formulation is intended for ophthalmic application, which is characterized by low incidence of systemic side effects because only a small amount of the dose will pass the retinal-blood barrier, no KET systemic adverse reactions are expected from this formulation. To examine the eye irritation upon application of the studied formulation, the rabbit eye irritation test was performed according to the method previously described by Zhu et al. (30) and Ammar et al (31). Twelve healthy New Zealand white rabbits weighing 1.5-2.5 kg were used. The rabbits were obtained from the animal house of the Faculty of Pharmacy, KAU, Jeddah, K S A. The protocol for this study received prior approval from the Animal Ethics Committee of the Faculty of Pharmacy, King Abdulaziz University, Jeddah, Saudi Arabia (Reference No 1021441). The work was conducted in adherence with the Declaration of Helsinki, the International Guiding Principle in Care and Use of Animals (DHEW production NIH 80-23), and the Standards of Laboratory Animal Care (NIH distribution #85-23, reconsidered in 1985). Before start of the experiment, rabbits were adapted for at least two weeks in a naturally controlled enclosures at 20° C.±1° C. with a 12/12-hour dark/light cycle. Libitum was added to standard food and water.

Rabbits were randomly classified into three groups consisting of four rabbits each. Group I received ocular treatment of 25 µL of nonmedicated carbopol-based ISG formulation (control group). Group II was administered the same volume of F3 (carbopol-based ISG formulation containing the optimized drug trans-ethosomes nanovesicles). The third group was given the same volume of F4 (carbopol-based ISG formulation containing pure KET). The studied formulations were instilled, using a micropipette, into the lower conjunctival sac. Eyes of the treated animals were observed over a period of 8 h. The degree of eye irritation was recorded following the classical Draize test (32).

Fluorescence Laser Microscope (FLM) Study

The transport of the prepared trans-ethosomes from the selected ISG formulation across the eye layers was investigated using a Zeiss Axio Observer D1 Inverted FLM of Carl Zeiss AG (Oberkochen, Germany). An optimized trans-ethosomes formulation loaded with fluorescence isothiocyanate (FITC), instead of KET, was prepared and loaded into carbopol-based ISG, as previously described. Also, a carbopol-based ISG formulation loaded with pure FITC was prepared as a control. A volume of 25 µL from each formulation was instilled, using a micropipette, into the lower conjunctival sac. Twelve healthy New Zealand white rabbits weighing 1.5-2.5 kg were used. The rabbits were randomly classified into two groups consisting of six rabbits each. The animals were sacrificed after 1, 2, and 4 h (n=2 rabbits per each endpoint/formula). Both eyes of each animal were removed immediately. The whole eyes were kept in formalin, and a longitudinal section across each sample using microtome blades was performed. Paraffin wax samples were prepared. Fluorescence laser microscopic images were taken using 470/40 nm excitation, 495 beam splitter, and 525/50 nm emission.

Results and Discussion

Optimization of the Trans-Ethosomal Nanoparticles

KET trans-ethosomes nanovesicles have been developed utilizing the thin film hydration technique. The prepared nanovesicles were characterized for size, PDI, zeta potential, entrapment efficiency, and flexibility. Table 2 demonstrates the obtained results of nanovesicles characterization for the 18 prepared formulations. The particle size was in the range 220.67±28.08 to 1063.33±131.96 nm, and the obtained zeta potential values were between 12.87±0.93 and 36.80±1.04 mV. The EE was in the range 42.27±1.35–94.52±2.84%, and the flexibility was between 63.83±0.44-96.24±2.44%. PDI of the prepared vesicles was in the range of 0.463±0.05 to 0.692±0.05, which is an indication of nanovesicles' homogeneity and acceptable size distribution. It has been previously reported that PDI values smaller than 0.05 are mainly observed with highly monodispersed systems, while PDI values greater than 0.7 specify a broad particle size distribution (33).

TABLE 2

Experimental runs of ketoconazole trans-ethosomes nanovesicles and the observed values for the studied responses.

| RUN | X1 MR | X2 % | X3 % | X4 % | Y1 nm | Y2 mV | Y3 % | Y4 % |
|---|---|---|---|---|---|---|---|---|
| 1  | 3    | 17.5  | 62.95 | 15    | 543.67 ± 2.08    | 29.80 ± 1.15 | 57 ± 4.16     | 80.76 ± 12.77 |
| 2  | 4.68 | 17.5  | 31    | 15    | 817.17 ± 20.74   | 29.03 ± 2.02 | 64.71 ± 2.20  | 75.15 ± 34.66 |
| 3  | 3    | 17.5  | 31    | 15    | 685.27 ± 85.33   | 29.03 ± 0.84 | 78.29 ± 3.60  | 77.96 ± 7.18  |
| 4  | 3    | 17.5  | 31    | 23.41 | 608.93 ± 54.51   | 36.80 ± 1.04 | 82.74 ± 3.20  | 78.13 ± 0.40  |
| 5  | 2    | 25    | 50    | 20    | 220.67 ± 28.08   | 34.67 ± 0.71 | 76.48 ± 14.39 | 92.68 ± 1.74  |
| 6  | 3    | 30.11 | 31    | 15    | 389.67 ± 48.50   | 26.07 ± 0.64 | 79.97 ± 0.27  | 96.24 ± 2.44  |
| 7  | 3    | 10    | 50    | 10    | 251.13 ± 18.02   | 15.03 ± 0.38 | 83.69 ± 4.83  | 73.34 ± 4.09  |
| 8  | 3    | 17.5  | 31    | 15    | 621.77 ± 6.60    | 28.83 ± 1.53 | 80.74 ± 0.81  | 80.05 ± 3.58  |
| 9  | 3    | 17.5  | 0     | 15    | 857.63 ± 151.99  | 29.13 ± 1.01 | 53.78 ± 48.53 | 70.93 ± 2.23  |
| 10 | 1.32 | 17.5  | 31    | 15    | 251.07 ± 114.12  | 30.37 ± 0.35 | 94.52 ± 2.84  | 73.83 ± 5.98  |
| 11 | 2    | 25    | 12    | 20    | 385.33 ± 72.71   | 34.60 ± 1.06 | 89.85 ± 2.85  | 83.48 ± 5.03  |
| 12 | 3    | 17.5  | 31    | 6.59  | 680.67 ± 11.06   | 12.87 ± 0.93 | 73.69 ± 5.21  | 74.87 ± 8.56  |
| 13 | 2    | 10    | 12    | 10    | 312.67 ± 52.08   | 13.83 ± 1.77 | 90.88 ± 2.51  | 69.85 ± 1.87  |
| 14 | 4    | 25    | 12    | 10    | 890.00 ± 94.30   | 15.17 ± 0.55 | 58.77 ± 1.97  | 89.30 ± 5.27  |
| 15 | 4    | 10    | 12    | 20    | 1061.00 ± 81.73  | 32.73 ± 0.67 | 48.04 ± 1.54  | 63.83 ± 0.44  |
| 16 | 4    | 10    | 50    | 20    | 817.00 ± 83.72   | 32.67 ± 0.91 | 42.27 ± 1.35  | 79.23 ± 0.67  |
| 17 | 4    | 25    | 50    | 10    | 317.63 ± 30.18   | 14.33 ± 0.76 | 48.44 ± 2.03  | 93.39 ± 3.28  |
| 18 | 3    | 4.89  | 31    | 15    | 1063.33 ± 131.96 | 25.77 ± 2.15 | 79.81 ± 9.21  | 69.69 ± 2.45  |

Abbreviations: X1, drug to phospholipid; X2, edge activator of the total lipid; X3, ethanol in the hydration medium; X4, stearyl amine of the total lipid; Y1, vesicle size; Y2, zeta potential; Y3, entrapment efficiency; Y4, flexibility; MR, molar ratio.

The obtained values for vesicle size, zeta potential, entrapment efficiency, and vesicle flexibility were statistically analyzed by multiple regression analysis and two-way analysis of variance (ANOVA) to identify the effect of $X_1$, $X_2$, $X_3$, and $X_4$ on $Y_1$, $Y_2$, $Y_3$, and $Y_4$. Regression analysis is a statistical tool that evaluates and analyzes the relationship between a dependent variable and one or more of the studied responses. ANOVA is used to study the main, interaction, and quadratic effect of $X_1$, $X_2$, $X_3$, and $X_4$ on $Y_1$, $Y_2$, $Y_3$, and $Y_4$. Hence, the estimated effect of factors, F-ratios, and P-values are calculated. A positive sign for the estimated effect indicates a synergistic effect of this factor on the studied response, while a negative sign denotes an antagonistic effect. The F-ratio is used to correlate the observed and expected averages. A value of the F-ratio greater than 1 indicates of a location effect; hence, the calculated P-value is used to specify if there is a significant level. A P-value that differs from zero and is less than 0.05 indicates a significant effect. Table 3 illustrates the obtained values for the estimated effect of factors, F-ratios, and the associated P-values.

TABLE 3

Estimated effects of factors, F-ratio, and associated P-values for KET-TEs formulations particle size ($Y_1$), zeta potential ($Y_2$), entrapment efficiency ($Y_3$) and flexibility ($Y_4$).

| Factor | $Y_1$ Estimated effect | $Y_1$ F-ratio | $Y_1$ P-value | $Y_2$ Estimated effect | $Y_2$ F-ratio | $Y_2$ P-value |
|---|---|---|---|---|---|---|
| $X_1$    | 336.606  | 12.94  | 0.037* | -0.797 | 0.160  | 0.713  |
| $X_2$    | -400.562 | 18.32  | 0.023* | 0.178  | 0.010  | 0.934  |
| $X_3$    | -230.007 | 14.58  | 0.032* | 0.219  | 0.030  | 0.874  |
| $X_4$    | -42.656  | 0.21   | 0.679  | 14.229 | 52     | 0.005* |
| $X_1X_1$ | -154.389 | 5.66   | 0.098  | -1.076 | 0.620  | 0.489  |
| $X_1X_2$ | -220.799 | 3.26   | 0.169  | -4.849 | 3.540  | 0.157  |
| $X_1X_3$ | -147.542 | 3.52   | 0.185  | -0.543 | 0.110  | 0.766  |
| $X_1X_4$ | -243.519 | 3.97   | 0.141  | -0.949 | 0.140  | 0.737  |
| $X_2X_2$ | -18.356  | 0.08   | 0.957  | -3.749 | 7.510  | 0.071  |
| $X_2X_3$ | -107.872 | 1.88   | 0.796  | -0.478 | 0.080  | 0.792  |
| $X_2X_4$ | -142.352 | 1.36   | 0.329  | 0.011  | 0      | 0.997  |
| $X_3X_3$ | -36.634  | 0.32   | 0.612  | 1.242  | 0.820  | 0.431  |
| $X_3X_4$ | 56.313   | 0.51   | 0.526  | -0.088 | 0      | 0.961  |
| $X_4X_4$ | -76.126  | 1.38   | 0.326  | -4.516 | 10.890 | 0.046* |
| $R^2$    |          | 97.21% |        |        | 98.52% |        |
| Adj-$R^2$|          | 84.16% |        |        | 91.64% |        |

| Factor | $Y_3$ Estimated effect | $Y_3$ F-ratio | $Y_3$ P-value | $Y_4$ Estimated effect | $Y_4$ F-ratio | $Y_4$ P-value |
|---|---|---|---|---|---|---|
| $X_1$ | -17.725 | 10.280 | 0.049* | 0.785  | 0.070  | 0.810  |
| $X_2$ | 0.095   | 0      | 0.987  | 15.787 | 27.790 | 0.013* |
| $X_3$ | -4.576  | 1.650  | 0.289  | 7.134  | 13.700 | 0.034* |

TABLE 3-continued

Estimated effects of factors, F-ratio, and associated P-values for KET-TEs formulations particle size ($Y_1$), zeta potential ($Y_2$), entrapment efficiency ($Y_3$) and flexibility ($Y_4$).

| | | | | | | |
|---|---|---|---|---|---|---|
| $X_4$ | 5.381 | 0.950 | 0.402 | 1.938 | 0.420 | 0.564 |
| $X_1X_1$ | −1.927 | 0.250 | 0.649 | −0.935 | 0.200 | 0.683 |
| $X_1X_2$ | 11.66 | 2.610 | 0.205 | 3.603 | 0.850 | 0.425 |
| $X_1X_3$ | 1.115 | 0.060 | 0.826 | 1.700 | 0.460 | 0.548 |
| $X_1X_4$ | −2.069 | 0.080 | 0.793 | −2.36 | 0.360 | 0.589 |
| $X_2X_2$ | −1.733 | 0.200 | 0.682 | 5.057 | 5.930 | 0.093 |
| $X_2X_3$ | −2.685 | 0.330 | 0.604 | −1.400 | 0.310 | 0.617 |
| $X_2X_4$ | 18.119 | 6.290 | 0.087 | −0.815 | 0.040 | 0.848 |
| $X_3X_3$ | −19.057 | 24.710 | 0.016* | 0.0235 | 0 | 0.992 |
| $X_3X_4$ | −0.405 | 0.010 | 0.936 | 4.255 | 2.850 | 0.189 |
| $X_4X_4$ | −2.917 | 0.580 | 0.502 | 0.486 | 0.050 | 0.830 |
| $R^2$ | | 97.11% | | | 97.24% | |
| Adj-$R^2$ | | 83.63% | | | 84.37% | |

Note:
*Indicates significant effect of factors on individual responses, P-value < 0.05.
Abbreviations: $X_1$, drug to phospholipid; $X_2$, edge activator of the total lipid; $X_3$, ethanol in the hydration medium; $X_4$, stearyl amine of the total lipid; $X_1X_2$, $X_1X_3$, $X_1X_4$, $X_2X_3$, $X_2X_4$, and $X_3X_4$ are the interaction terms between the factors; $X_1X_1$, $X_2X_2$, $X_3X_3$, and $X_4X_4$ are the quadratic terms of the factors; $R^2$, R-squared; Adj-$R^2$, adjusted R-squared; SEE, standard error of estimate; MAE, mean absolute error.

Influence of the Independent Variables ($X_1$-$X_4$) on the Particle Size ($Y_1$)

Statistical analysis for the effect of $X_1$-$X_4$ on the particle size ($Y_1$) indicated that the drug-to-phospholipid molar ratio ($X_1$), the percentage of the edge activator of the total lipid ($X_2$), and the percentage of ethanol in the hydration medium ($X_3$) had a significant effect on the particle size at P-values of 0.037, 0.023, and 0.032, respectively. These results were also confirmed after investigation the Pareto chart depicted in FIG. 1. The polynomial equation that relates $X_1$-$X_4$ and $Y_1$ is as follows:

$$(Y_1) = -3010.59 + 1374.71X_1 + 63.370X_2 + 10.919X_3 + 138.493X_4 - 77.195X_1^2 - 14.719X_1X_2 - 3.883X_1X_3 - 24.352X_1X_4 - 0.163X_2^2 - 0.379X_2X_3 - 1.898X_2X_4 - 0.051X_3^2 + 0.296X_3X_4 - 1.523X_4^2 \quad (1)$$

To demonstrate the effect of changing the levels of two factors on $Y_1$, when the other two factors were kept at their intermediate levels, three-dimensional (3D) response surface plots were constructed and are graphically illustrated in FIG. 2.

Upon increasing the drug-to-phospholipid molar ratio ($X_1$) from 1:2 to 1:4, the particle size was increased. This effect could be attributed to the formation of multilamellar vesicles, as previously described by Harbi et al. (34) and Ahmed (35). The percentage of the edge activator of the total lipid ($X_2$) antagonistically affected the particle size owing to the reduction in the surface tension of the media, which leads to phospholipid arrangement in small vesicles (24,36). Also, the percentage of ethanol in the hydration medium showed an antagonistic effect on the particle size, an effect that may be attributed to the formation of a phase with an interpenetrating hydrocarbon chain, which leads to a significant reduction in the membrane thickness (37). Another possible explanation for this effect is the reduction in the main transition temperature of the phospholipids, which results in partial fluidization of the prepared vesicles and formation of small nanoparticles upon increasing the ethanol content (38). The obtained $R^2$ value showed that the model as fitted explains 97.21% of the variability on the particle size, while the adjusted $R^2$ value, which is more appropriate for comparing models with different independent variables, was 84.16%.

Influence of the Independent Variables ($X_1$-$X_4$) on Zeta Potential ($Y_2$)

The percentage of stearyl amine of the total lipid ($X_4$) and its quadratic effect ($X_4X_4$) had a significant effect on the zeta potential ($Y_2$) at P-values of 0.005 and 0.046, respectively. The Pareto chart shown in FIG. 1 confirms this finding. The mathematical model for the zeta potential was generated, and the polynomial equation that best fit the model is $$(Y_2) = -51.045 + 10.352X_1 + 2.198X_2 + 0.191X_3 + 4.429X_4 + 0.538X_1^2 - 0.323X_1X_2 - 0.014X_1X_3 - 0.095X_1X_4 - 0.033X_2^2 - 0.002X_2X_3 + 0.001X_2X_4 - 0.002X_3^2 - 0.0005X_3X_4 - 0.0911X_4^2 \quad (2)$$

FIG. 3 shows the 3D estimated response surface plots for the effect of changing two factors, on zeta potential ($Y_2$), when the other two factors were kept at their intermediate levels.

All the prepared trans-ethosomes nanovesicles showed positive zeta potential values that were significantly affected by the percentage of stearyl amine of the total lipid ($X_4$). As the concentration of stearyl amine was increased, the obtained zeta potential value was increased owing to further deposition of the charge-inducing agent on the vesicles' outer surface. A previous study indicated an increase in the zeta potential value of positively charged rosuvastatin flexible liposomes upon increasing the concentration of the coating positively charged polymer (chitosan) (35). The obtained $R^2$ value showed that the model as fitted explains 98.52% of the variability on zeta potential, while the adjusted $R^2$ value, which is more appropriate for comparing models with different independent variables, was 91.64%.

Influence of the Independent Variables ($X_1$-$X_4$) on the Entrapment Efficiency ($Y_3$)

It was noted from the ANOVA that the main effect of the drug-to-phospholipid molar ratio ($X_1$) and the quadratic effect of the ethanol percentage in the hydration medium ($X_3X_3$) had a significant effect on the EE at P-values of 0.049 and 0.016, respectively. This finding was also confirmed after studying the Pareto chart illustrated in FIG. 1. The polynomial equation that correlates the studied independent variables and the entrapment efficiency ($Y_3$) is $$(Y_3) = 142.860 - 14.497X_1 - 5.119X_2 + 1.625X_3 - 1.253X_4 - 0.964X_1^2 + 0.778X_1X_2 + 0.029X_1X_3 - 0.207X_1X_4 - 0.015X_3^2 - 0.009X_2X_3 + 0.242X_2X_4 - 0.026X_3^2 - 0.002X_3X_4 - 0.058X_4^2 \quad (3)$$

The effect of changing two factors on the EE ($Y_3$) when the other two factors were kept at their intermediate levels is shown in FIG. 4.

The EE of the prepared nano-vesicles was significantly affected by the drug-to-phospholipid molar ratio ($X_1$) in an antagonistic way; this effect could be attributed to the decrease in the drug load of the prepared nanovesicles upon increasing $X_1$. This finding was also observed during development of α-tocopherol liposomal formulation. The authors reported that the drug encapsulation efficiency was dramatically decreased when using α-tocopherol-to-phospholipid molar ratios of 1:10 or more (39). In another study, the effect of changing the drug to a phospholipid molar ratio on the EE of sildenafil-loaded transferosomes was studied. The author reported an initial increase in the EE when the amount of lipid was increased; however, further increase in the amount of lipid resulted in a decrease in the drug EE. The author attributed this finding to the competition between the drug and the phospholipid at high lipid load (40). The obtained $R^2$ value showed that the model as fitted explains 97.11% of the variability on the entrapment efficiency, while the adjusted $R^2$ value was found to be 83.63%.

Influence of the Independent Variables ($X_1$-$X_4$) on Flexibility ($Y_4$)

ANOVA revealed a marked significant effect of $X_2$ (the edge activator of the total lipid, P-value=0.013) and $X_3$ (the ethanol in the hydration medium, P-value=0.034) on the flexibility ($Y_4$). The polynomial equation of the model is $$(Y_4)=71.769+1.153X_1-0.926X_2-0.198X_3+0.107X_4-0.468X_1^2+0.240X_1X_2+0.045X_1X_3-0.236X_1X_4+0.045X_2^2-0.005X_2X_3-0.011X_2X_4+0.00003X_3^2+0.022X_3X_4+0.009X_4^2 \quad (4)$$

The effect of the studied factors on the flexibility of the prepared nanovesicles is illustrated in the 3D response surface plots (FIG. 5).

Upon increasing the edge activator ($X_2$) and the ethanol concentration in the hydration medium ($X_3$), flexibility of the vesicles was increased. The effect of $X_2$ may be attributed to the insertion of more surfactant molecules into the membrane of the vesicles with the lipophilic part (oleate residue) arranged parallel to the acyl chains of the phospholipid and the hydrophilic head (polyoxyethylene units) directed toward the head group of the phospholipids, which leads to the nanovesicles' flexibility (41). The effect of $X_3$ could be related to partial fluidization of the prepared vesicles, as discussed above. Another possible explanation for the effect of ethanol concentration is the decrease in the interfacial tension of the vesicle membrane upon increasing the ethanol concentration (42). The obtained $R^2$ value showed that the model as fitted explains 97.24% of the variability on the vesicle flexibility, while the adjusted $R^2$ value was 84.37%.

Development of the Optimized Trans-Ethosomal Formulation

Based on the multiple response statistical analysis for the obtained data, the optimum desirability that achieve the study's goals are $X_1$, $X_2$, $X_3$, and $X_4$ levels of 1.71, 28.69, 42.76, and 23.36, respectively. An optimized KET trans-ethosomes formulation that contains these values was prepared and characterized for $Y_1$-$Y_4$, as previously mentioned. The optimized drug-loaded trans-ethosomes formulation showed an average size of 151.34±8.73 nm, a PDI value of 0.511±0.057, a zeta potential value of +34.82±2.64 mV, an EE of 94.97±5.41%, and a flexibility of 95.44±4.33%. The predicted values for $Y_1$, $Y_2$, $Y_3$, and $Y_4$ were 157.67 nm, +36.82 mV, 96.85%, and 96.07%, respectively.

Morphological Study of the Trans-Ethosomal Nanoparticles

Figures 6A, 6B:
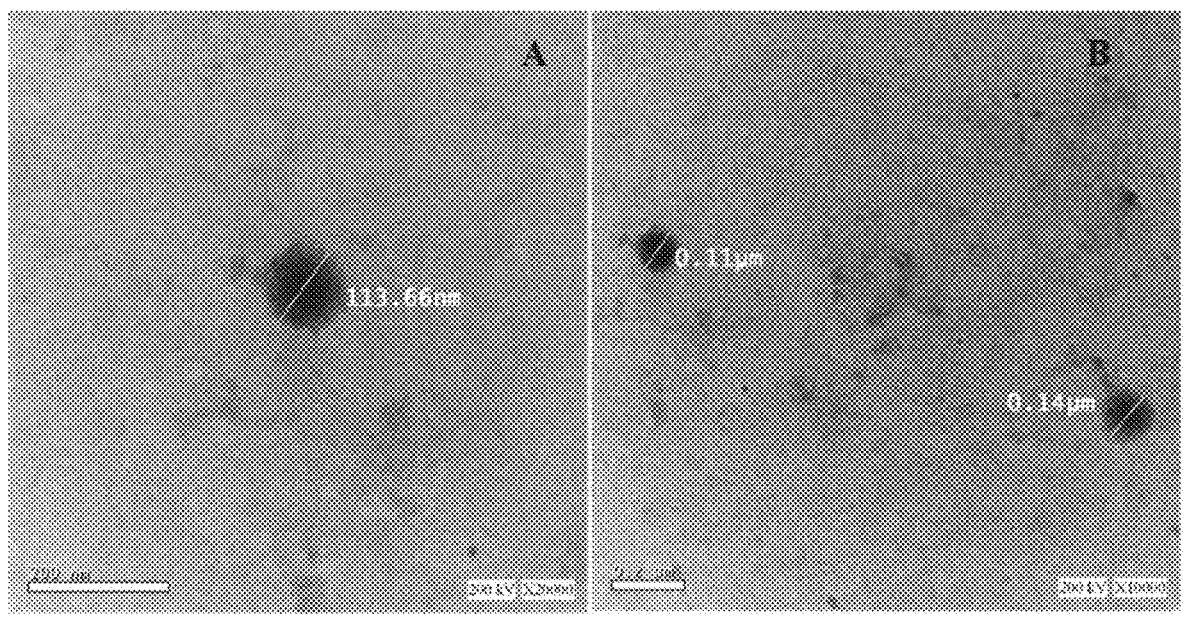
FIGS. 6A-B. Transmission electron microscope for the optimized trans-ethosomal nanoparticles at 20000× (A) and 10000× (B).

TEM image for the optimized trans-ethosomes formulation revealed spherical-shaped vesicles, as depicted in FIG. 6. The size of the vesicles displayed in the TEM image was smaller than that obtained by the dynamic light-scattering technique using the Malvern Zetasizer. This finding could be attributed to the solvent-removal effect during sample preparation for TEM imaging, which may cause size modifications. This explanation has been previously described by Das and Chaudhury, which illustrated that the sample preparation (e.g., solvent removal) may directly affect the particle size and shape (43). The same finding was also mentioned during size determination and morphological characterization of finasteride microplates (44).

Solid-State Physicochemical Characterization

Differential Scanning Calorimetry

The DSC thermogram of pure KET revealed a distinguishing sharp endothermic peak at 150.47° C. L-α phosphatidylcholine showed a phase transition temperature at about 48° C. corresponding to the chain-melting transition. When the phospholipid sample was heated above the transition temperature, the phospholipid molecules were arranged in a multilayered liquid-crystalline phase structure, which exhibits a greater degree of motional freedom and undergoes several thermo-tropic transitions above the phospholipid phase transition temperature and below the isotropic melts (which usually occurs at about 230° C. for most phospholipids) (45). This behavior was obvious in the DSC thermogram of the studied phospholipid (FIG. 7), which exhibited a major thermo-tropic transition peak at about 190° C. The freeze-dried optimized drug-loaded formulation showed a slight shift in the drug peak to 156.73° C. and in the phospholipid major thermo-tropic transition peak to 166.80° C. This finding indicates the molecular dispersion of the drug in the optimized trans-ethosomes formulation.

FT-IR Spectroscopy

Figure 8:
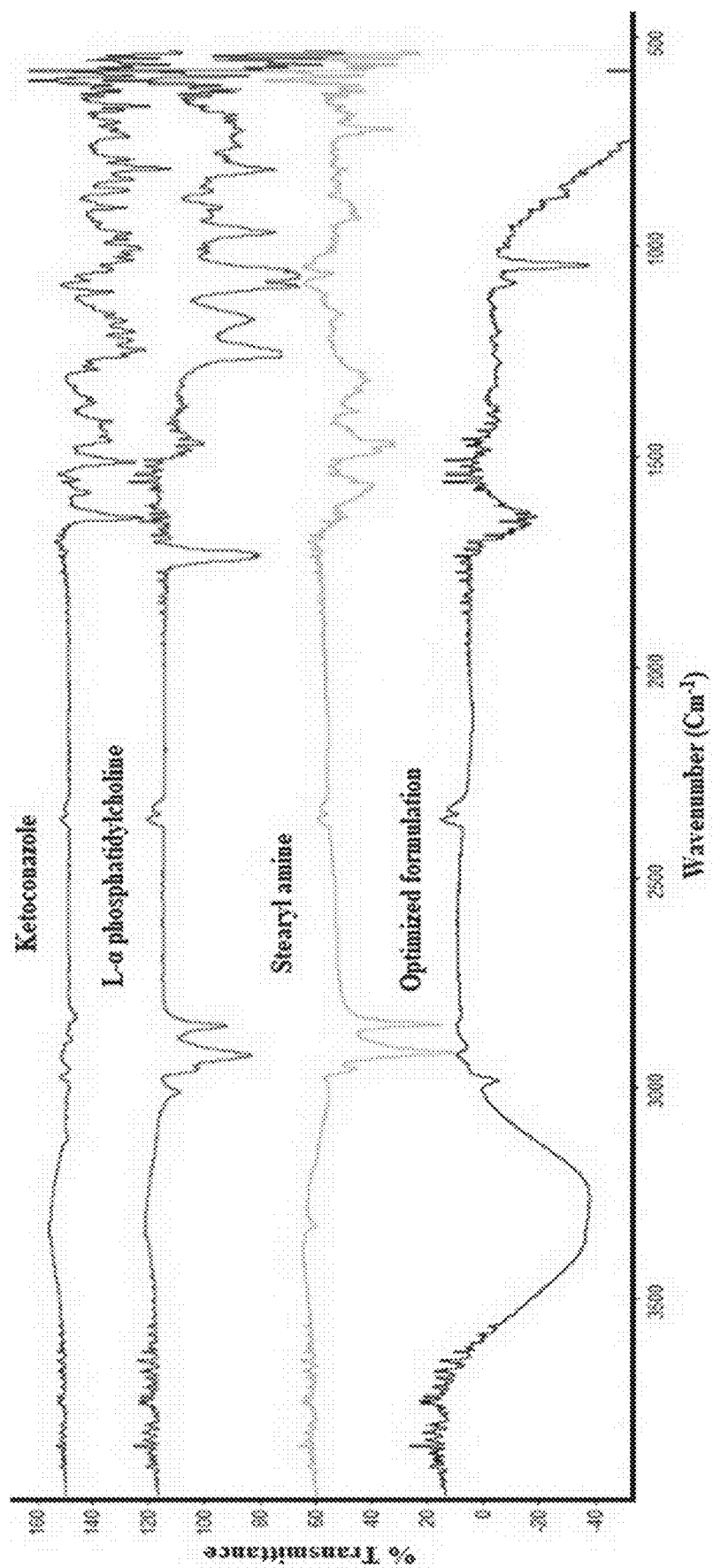
FIG. 8. Fourier transform infrared spectra of ketoconazole, phospholipid, stearyl amine, and the freeze-dried optimized formulation.

The FT-IR spectrum (FIG. 8) of KET demonstrated a characteristic drug peak of the carbonyl group [C=O] stretching vibration at 1,647.26 cm$^{-1}$. Other characteristic drug peaks for the C—O stretching of the cyclic ether and C—O stretching of the aliphatic ether group were observed at 1244 and 1,031.95 cm$^{-1}$, respectively. The FT-IR spectrum of the studied phospholipid demonstrated a vibration band at 1200-1145 cm$^{-1}$ due to the P02 group vibration. Another band for the carbonyl group (C=O) was observed at 1765-1720 cm$^{-1}$ (46). The C—H bands of the phospholipid were detected at 2,925 and 2,855 cm$^{-1}$ (47). Stearyl amine displayed a maximum absorbance around 2,925 and 2,855 cm$^{-1}$ due to the C—H bands. The characteristic C—N stretch of stearyl amine was detected at 1,300 cm$^{-1}$, as a sharp medium intensity peak and the NH$_2$ wagging vibration were observed at 600 cm$^{-1}$ (47). The spectra of the optimized trans-ethosomes formulation showed a new significant broad stretch that appeared at 3,050-3,500 cm$^{-1}$, corresponding to the O—H group, which formed during the electrostatic interaction between the amino group of the stearyl amine and the carbonyl group of the phospholipid. This finding was previously mentioned by Zidan et al. during development of tenofovir liposomes formulation (47). This electrostatic interaction was also confirmed by the disappearance of the phospholipid carbonyl group, which was observed between 1765-1720 cm$^{-1}$. The spectra of the optimized formulation also showed a decrease in the intensity, slight shift, and some overlapping in the characteristic peaks of the drug, the phospholipid, and stearyl amine Accordingly, formation of a lipid-based nanovesicles with a modified charged surface that enclose KET is most likely to occur.

X-Ray Powder Diffraction

FIG. 9 illustrates the XRPD patterns of pure KET and the optimized freeze-dried nanovesicles' formulation. The pure drug demonstrated a crystalline nature as specified by the presence of numerous and sharp peaks in its diffraction spectrum. This behavior was changed in the diffraction pattern of the freeze-dried optimized nanovesicles' formulation. There was a decrease in the intensity, disappearance, and development of some peaks, which is an indication of crystalline transformation and change in the drug nature from crystalline to amorphous.

Antifungal Activity of KET Trans-Ethosomes Nanoparticles

The antifungal activity of the optimized KET loaded trans-ethosomes nanovesicles (test) was compared with a drug suspension (positive control) and to a plain trans-ethosomes formulation (negative control). A great antifungal activity, as indicated by a large inhibition zone, was observed in the dish treated with the optimized KET-loaded trans-ethosomes formulation (26 mm). Small inhibition was noted in the dish treated with the drug suspension (11 mm), and no inhibition (0 mm) was observed after treatment with the plain (nonmedicated) trans-ethosomes nanovesicles. These results indicate improvement in KET antifungal activity upon loading into trans-ethosomes nanovesicles, which enhanced the drug diffusion, as previously mentioned for KET-loaded polymeric poly(lactide-co-glycolide) nanoparticles (5).

significant effect on the formulation viscosity. Higher viscosity value was observed with ISG formulations containing sodium alginate (F5-F6), followed by ISG formulations containing carbopol (F3-F4), and finally ISG formulations containing poloxamer (F1-F2). This finding is in a good agreement with a previous work of Basaran and Bozkir who developed ophthalmic ISG formulations of ciprofloxacin hydrochloride using poloxamer and carbopol polymers (16). Unlike the ISG, hydrogels are simple viscous solutions that cannot undergo any modification after administration (49). The prepared hydrogel formulations (F7-F8) showed higher viscosity value than the corresponding ISG formulations. Both formulations are used to prolong drug release, reduce frequency of application, and reduce the systemic effect due to the nature of these formulations' viscosities. Low viscosity before gelling has been reported to be suitable for ophthalmic application. A viscosity value up to 3500 cP (at 25° C. and 10 rpm) has been mentioned to be appropriate in term of applying convenience (16). Song et al. reported satisfactory viscosity values of 700±85, 1120±49, and 4300±120 mPa s (at 20 rpm) at pH 5.5, 6, and 7, respectively, for carbopol/HPMC ocular ISG system (50).

TABLE 4

Composition of the prepared ophthalmic in situ gels and hydrogels formulations and the obtained results for viscosity.

| Formulation | | Type of Polymers | Polymer Conc. (%) | Drug Form | Viscoity (cP) (25° C., 30 rpm) | Viscosity (cP) After Gelation | Gelation Stimuli |
|---|---|---|---|---|---|---|---|
| ISG | F1 | Poloxamer 407 | 16 | KET-TNV | 657 ± 49 | 17863 ± 891 | Temperature change (34° C.) |
| | | HPMC | 0.5 | | | | |
| | F2 | Poloxamer 407 | 16 | PD | 477 ± 33 | 10465 ± 680 | Temperature Change (34° C.) |
| | | HPMC | 0.5 | | | | |
| | F3 | Carbopol 940 | 1 | KET-TNV | 967 ± 47 | 26109 ± 1821 | pH change (to 7.4) |
| | | HPMC | 0.5 | | | | |
| | F4 | Carbopol 940 | 1 | PD | 853 ± 51 | 22031 ± 1106 | pH change (to 7.4) |
| | | HPMC | 0.5 | | | | |
| | F5 | Sodium alginate | 1 | KET-TNV | 1515 ± 81 | 39390 ± 1771 | Ionic gelation (CaOH) |
| | | HMPC | 0.5 | | | | |
| | F6 | sodium alginate | 1 | PD | 1262 ± 82 | 31550 ± 1557 | Ionic gelation (CaOH) |
| | | HPMC | 0.5 | | | | |
| Hydrogel | F7 | HPMC | 2 | KET-TNV | 1470 ± 88 | — | — |
| | F8 | HPMC | 2 | PD | 1361 ± 75 | — | — |

Abbreviations: ISG, in situ gel; KET-TNV, ketoconazole trans-ethosomes nanovesicles; PD, pure ketoconazole.

A previous study indicated that the minimum inhibitory concentration value of KET against yeast isolates obtained from cases of keratitis is 0.015-0.125 μg/ml (48). In this study, the optimized trans-ethosomes dispersion loaded with 0.1% w/v KET, which showed an EE of 94.97±5.41%, was found to be an effective antifungal preparation.

Characterization of Ophthalmic Preparations Loaded with KET Trans-Ethosomes

Rheological Properties

All the studied formulations exhibited a decrease in viscosity upon increasing the shear stress, which is an indication of a pseudoplastic behavior. The ISG formulations were liquid at room temperature (25° C.) and transformed rapidly into the gel phase upon exposure to the gelation stimuli (increasing the temperature to 34° C., raising the pH to 7.4, or adding 0.5 M CaOH). These stimuli were used to mimic the eye biological condition. The type of polymer used to develop the ISG formulation exhibited a In Vitro Release Study Previous reports indicated that the volume of a human's tear is about 7 μL, and the cul-de-sac can accommodate a volume of fluid ~30 μL (51). Accordingly, known volume of the formulation and the STF in a ratio of 25:7 (formulation: STF) was used during this experiment.

All the studied ophthalmic preparations demonstrated an extended drug release over 6 h. The release of KET was higher from the trans-ethosomes nanovesicles compared with the same ophthalmic preparations containing pure drug, as depicted in FIG. 10. This behavior is mainly attributed to the smaller particle size of the developed trans-ethosomes when compared with the size of the pure drug suspension, which is expected to be in the form of coarse dispersion. Higher cumulative drug release percentage was obtained from F3 (101.65±5.95%), F1 (71.12±5.15%), F3 (66.71±4.95%), F7 (63.49±7.19%), F4 (59.78±9.42%), F6 (50.89±6.38%), F2 (46.48±6.39%), and finally F8

(43.75±5.38%). These results indicate a higher cumulative drug release from the carbopol-based formulation—the effect that could be attributed to easy diffusion of KET from this system.

Upon fitting the obtained data of the in vitro drug release to various kinetic models, all the studied formulations followed zero-order kinetics, as indicated by the highest value of the correlation coefficient (R) of the model, which is an indication that the release of KET was independent of the amount of drug released at different time points. The obtained results are in a good agreement with previous work that reported zero-order release kinetics for itraconazole from polymeric micelles incorporated in situ ocular gel (52). The (n) exponent obtained from the slope of the figure of log fraction of KET released (Mt/Moo) versus time demonstrated that the release mechanism follows anomalous (non-Fickian) transport (n>0.45), which is a combination of both diffusion and erosion controlled-drug release.

It must be mentioned that biodegradability is one of the characteristics that makes the studied polymers beneficial for use in ophthalmic drug delivery (53). Carbopol improves the precorneal retention time of the applied drug. It provides the benefit of excellent mucoadhesive properties, as compared with other polymers, and high drug release. Its mucoadhesive properties is attributed to the interaction of the carbopol poly(acrylic acid) with the mucin by a combination of hydrogen bonding and electrostatic interaction (54). A carbopol-based in situ gel demonstrated improved ophthalmic brinzolamide bioavailability and showed an extended drug release over a period of 8 h (55). Good correlation between carbopol biodegradability and drug release has been previously mentioned. Incorporation of HPMC in the formulation decreases irritation and eye damage, which occurs due to the acidic nature of the prepared gel (56). A combination of carbopol 940 (0.1% w/v), used as a gelling agent, and HPMC (0.4% w/v), used as viscosity modifier, was used to develop an ISG system, which has demonstrated acceptable gel strength, sustained drug release over a period of 8 h, no ocular toxicity or irritancy, in vivo elimination within 25 min, and effective suppression of inflammation for uveitis treatment (50). Accordingly, the carbopol-based ISG formulation was selected for further investigation.

In Vivo Ocular Irritation Test

The eye irritation test on New Zealand white rabbits showed that the studied carbopol-based ISG formulations were nonirritants and could be tolerated. No macroscopic signs of swelling, redness, abnormal secretions, corneal opacity, congestion, hemorrhage, or marked destruction appeared in the iris. All animal eyes looked normal when compared with the control. Accordingly, the carbopol-based ISG formulations achieved a total score of zero in the irritation assessment using the classical Draize test and are considered as safe preparations for ocular administration. The same finding was previously reported for thermosensitive ISG formulation of pure KET (30). Microscopic investigation of the corneal structure and integrity of the eye tissues will be discussed in the following section.

Fluorescence Laser Microscope Study

Figure 11:
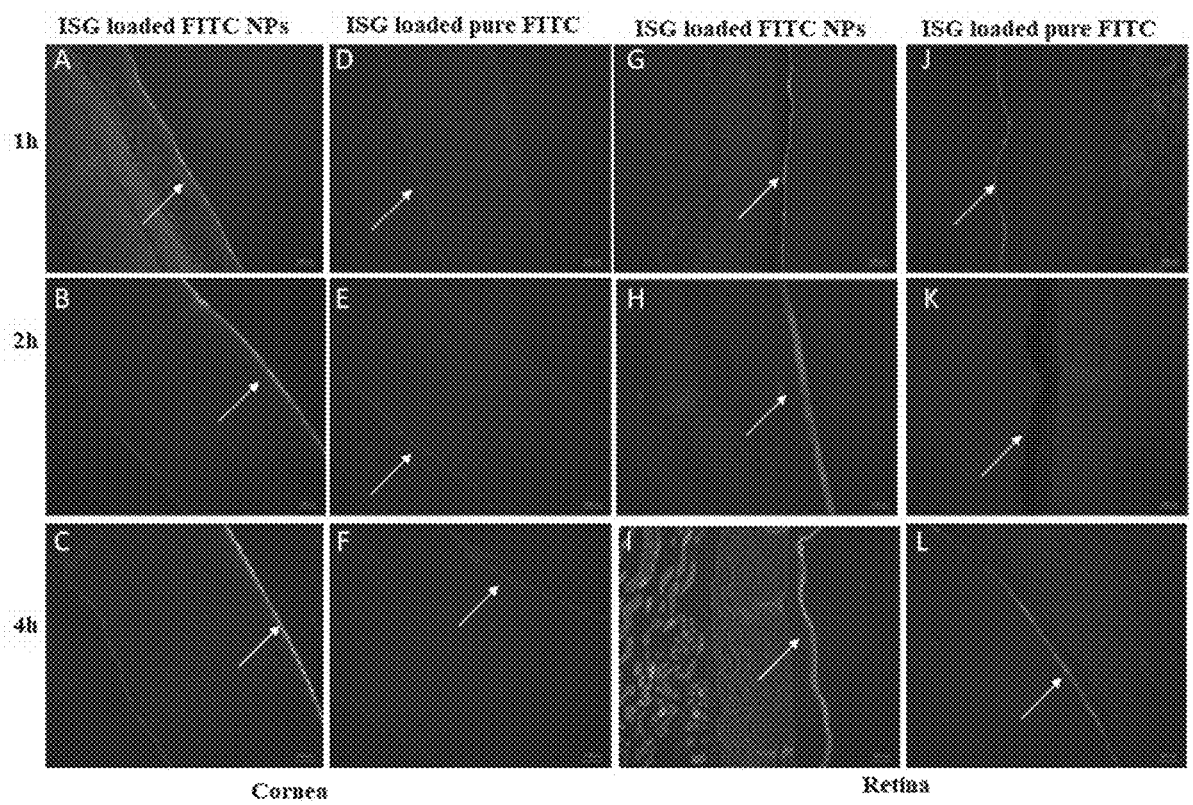
FIG. 11. Fluorescence laser microscopic images of the eye's sections on New Zealand white rabbits' eyes following treatment with ISG formulation containing FITC-nanovesicles and ISG formulation loaded with pure FITC after 1, 2, and 4 h. Sections of the cornea (A-F) and retina (G-L) of rabbits' eyes from both groups (arrows point to the fluorescent).

To examine the diffusion of the developed nanovesicles from the prepared carbopol-based ISG across the eye, the transport of these nanovesicles loaded with FITC from the anterior to the posterior part of the eye was studied. FIG. 11 illustrates fluorescence laser microscopic images in the anterior part (cornea) and the posterior part (retina) of a rabbit's eyes following treatment with the studied formulations. The fluorescence of the dye was clearly observed in the cornea of rabbits treated with the ISG formulation loaded with FTIC nanovesicles. The fluorescence was noted in the corneal samples at all the studied time points (after 1, 2, and 4 h). On the other hand, little fluorescence was observed in the cornea of the ISG loaded with pure FITC due to the limited distribution of the pure dye in the corneal cells. The retina of the animals treated with the IS G formulation loaded with nanovesicles containing FTIC demonstrated good distribution of the nanovesicles to the posterior part of the eye, as indicated by the presence of fluorescence in all the studied samples. Further, the fluorescence of the dye was hardly seen in the retina of the rabbits treated with ISG formulation loaded with pure FITC. It must be mentioned that FITC is of a limited solubility in water (less than 0.1 mg/ml in water); thus, it was coarsely dispersed in the ISG matrix of the ISG formulation loaded with the pure dye. This effect may result in rapid washing of the dye by the tears and the eye-blinking action and, thus, account for poor distribution of the pure dye in the corneal cells. The successful permeation of some of the pure dye particles to the retina may be attributed to the long contact of the ISG formulation with the eye.

The obtained results indicate successful delivery of the nanovesicles to the posterior eye segment and may account for the effectiveness of this formulation in treatment of fungal retinitis. Our results are in good agreement with previous work that reported the presence of a significantly higher KET concentration in the aqueous and vitreous humor following administration of drug solid lipid nanoparticles (SLNs) when compared with pure drug suspension. The authors mentioned that the prepared drug SLNs may indirectly establish their effectiveness in treatment of fungal retinitis and attributed this effect to the fact that more than 70% of the fluid in the vitreous humor moves toward and exits through the retina (57). Our work is more advantageous since the prepared nanoparticles were successfully delivered to the retina. Finally, the observed corneal structure and integrity were unaffected by the formulation treatment. No side effects were noted upon incorporation of ethanol in the development of ophthalmic preparation loaded with transethosomes nanovesicles. These results are in a good agreement with those of the previous studies, which indicated the use of ethanol in ocular surface surgeries and in the treatment of different corneal diseases (13). It is previously stated that the rabbit eye is more susceptible to irritant substances than the human eye (58). Accordingly, the prepared carbopol-based ISG formulation loaded with the optimized KET would also be an effective ophthalmic delivery system in the treatment of fungal infections.

CONCLUSIONS

Optimized KET trans-ethosomes nanovesicles were successfully developed utilizing the Draper-Lin small composite design. The optimized trans-ethosomes were spherical in shape and illustrated cationic nanosized flexible particles of high drug entrapment efficiency. The optimized nanovesicles showed superior antifungal activity against a standard strain of *Candida albicans* when compared with a drug suspension and a plain trans-ethosomes formulation. Different ophthalmic formulations loaded with the optimized trans-ethosomes were developed and showed prolonged drug release, no irritation on the eyes of the New Zealand white rabbits, and were able to permeate deep into the posterior eye segments. Thus, this ophthalmic KET delivery system could be used to enhance the drug ocular permeation, rapid eye clearance, and short elimination half-life in the eye.

ACKNOWLEDGMENT

The Deanship of Scientific Research (DSR) at King Abdulaziz University, Jeddah, Saudi Arabia has funded this project, under grant no. (RG-23-166-42).

REFERENCES

1. Klotz S A, Penn C C, Negvesky G J, Butrus S I. Fungal and parasitic infections of the eye. Clinical Microbiology Reviews. 2000.
2. Meier P, Wiedemann P Endophthalmitis—Clinical appearance, therapy and prevention. Vol. 210, Klinische Monatsblatter fur Augenheilkunde. Georg Thieme Verlag; 1997. p. 175-91.
3. Park H J, Kim S H, Ju H W, Lee H, Lee Y, Park S, et al. Microplasma Jet Arrays as a Therapeutic Choice for Fungal Keratitis. Sci Rep. 2018 Dec. 1; 8(1).
4. Stern W H, Tamura E, Jacobs R A, Pons V G, Stone R D, O'Day D M, et al. Epidemic Postsurgical Candida Parapsilosis Endophthalmitis: Clinical Findings and Management of 15 Consecutive Cases. Ophthalmology [Internet]. 1985 [cited 2020 Nov. 3]; 92(12):1701-9.
5. Ahmed T A, Aljaeid B M. A potential in situ gel formulation loaded with novel fabricated poly(Lactide-co-glycolide) nanoparticles for enhancing and sustaining the ophthalmic delivery of ketoconazole. Int J Nanomedicine. 2017; 12:1863-75.
6. Ashley E S D, Lewis R, Lewis J S, Martin C, Andes D. Pharmacology of systemic antifungal agents. Clin Infect Dis. 2006; 43(SUPPL. 1).
7. Choi F D, Juhasz M L W, Atanaskova Mesinkovska N. Topical ketoconazole: a systematic review of current dermatological applications and future developments [Internet]. Vol. 30, Journal of Dermatological Treatment. Taylor and Francis Ltd; 2019 [cited 2020 Dec. 22]. p. 760-71.
8. Ranpise H A, Gujar K N, Pawar S C, Awasthi R, Dua K, Mathure D, et al. Formulation, Optimization, and Evaluation of Ketoconazole Loaded Nanostructured Lipid Carrier Gel for Topical Delivery. Drug Deliv Lett [Internet]. 2020 Feb. 12 [cited 2020 Dec. 22]; 10(1):61-71.
9. Thakkar R, Patil A, Mehraj T, Dudhipala N, Majumdar S. Updates in Ocular Antifungal Pharmacotherapy: Formulation and Clinical Perspectives [Internet]. Vol. 13, Current Fungal Infection Reports. Current Medicine Group LLC 1; 2019 [cited 2020 Dec. 22]. p. 45-58.
10. Nagasamy Venkatesh D, Balamurugan S D, Manisha M, Bhowmik H. Formulation and Characterization of Ketoconazole Loaded Nanosponges in Hydrogel for Treating Topical Fungal Infections. In: Conference on Drug Design and Discovery Technologies [Internet]. 2019 [cited 2020 Dec. 22]. p. 340-50.
11. Rao Y, Zheng F, Zhang X, Gao J, Liang W. In vitro percutaneous permeation and skin accumulation of finasteride using vesicular ethosomal carriers. AAPS PharmSciTech [Internet]. 2008 January [cited 2016 Feb. 13]; 9(3):860-5.
12. Gupta P N, Mishra V, Rawat A, Dubey P, Mahor S, Jain S, et al. Non-invasive vaccine delivery in transfersomes, niosomes and liposomes: A comparative study. Int J Pharm. 2005; 293(1-2):73-82.
13. Oh J Y, Yu J M, Ko J H. Analysis of ethanol effects on corneal epithelium. Investig Ophthalmol Vis Sci. 2013; 54(6):3852-6.
14. Youssef A, Dudhipala N, Majumdar S. Ciprofloxacin loaded nanostructured lipid carriers incorporated into in-situ gels to improve management of bacterial endophthalmitis. Pharmaceutics. 2020; 12(6):1-19.
15. Tatke A, Dudhipala N, Janga K Y, Balguri S P, Avula B, Jablonski M M, et al. In situ gel of triamcinolone acetonide-loaded solid lipid nanoparticles for improved topical ocular delivery: Tear kinetics and ocular disposition studies. Nanomaterials. 2019; 9(1):1-17.
16. Başaran B, Bozkir A. Thermosensitive and pH induced in situ ophthalmic gelling system for ciprofloxacin hydrochloride: Hydroxypropyl-β-cyclodextrin complex. Acta Pol Pharm—Drug Res. 2012; 69(6):1137-47.
17. Gupta S, Vyas S P. Carbopol/Chitosan Based pH Triggered In Situ Gelling System for Ocular Delivery of Timolol Maleate. Sci Pharm [Internet]. 2010 [cited 2016 Nov. 18]; 78:959-76.
18. Song C K, Balakrishnan P, Shim C K, Chung S J, Chong S, Kim D D. A novel vesicular carrier, transethosome, for enhanced skin delivery of voriconazole: Characterization and in vitro/in vivo evaluation. Colloids Surfaces B Biointerfaces. 2012; 92:299-304.
19. Albash R, Abdelbary A A, Refai H, El-Nabarawi M A. Use of transethosomes for enhancing the transdermal delivery of olmesartan medoxomil: In vitro, ex vivo, and in vivo evaluation. Int J Nanomedicine. 2019; 14:1953-68.
20. Janga K Y, Tatke A, Dudhipala N, Balguri S P, Ibrahim M M, Maria D N, et al. Gellan gum based sol-to-gel transforming system of natamycin transfersomes improves topical ocular delivery. J Pharmacol Exp Ther. 2019; 370(3):814-22.
21. Ahmed T A, El-Say K M, Aljaeid B M, Fahmy U A, Abd-Allah F I. Transdermal glimepiride delivery system based on optimized ethosomal nano-vesicles: Preparation, characterization, in vitro, ex vivo and clinical evaluation. Int J Pharm [Internet]. 2016; 500(1-2):245-54.
22. Pitta S K, Dudhipala N, Narala A, Veerabrahma K. Development of zolmitriptan transfersomes by Box-Behnken design for nasal delivery: in vitro and in vivo evaluation. Drug Dev Ind Pharm. 2018; 44(3):484-92.
23. Dudhipala N, AY A A. Amelioration of ketoconazole in lipid nanoparticles for enhanced antifungal activity and bioavailability through oral administration for management of fungal infections. Chem Phys Lipids. 2020 Oct. 1; 232:104953.
24. Alomrani A, Badran M, Harisa G I, ALshehry M, Alhariri M, Alshamsan A, et al. The use of chitosan-coated flexible liposomes as a remarkable carrier to enhance the antitumor efficacy of 5-fluorouracil against colorectal cancer. Saudi Pharm J [Internet]. 2019 Jul. 1 [cited 2020 Nov. 16]; 27(5):603-11.
25. Wagner J G. Interpretation of percent dissolved-time plots derived from in vitro testing of conventional tablets and capsules. J Pharm Sci [Internet]. 1969 October [cited 2015 Apr. 26]; 58(10):1253-7.
26. Higuchi T. Mechanism of sustained-action medication. Theoretical analysis of rate of release of solid drugs dispersed in solid matrices. J Pharm Sci [Internet]. 1963 December [cited 2015 Apr. 26]; 52:1145-9.
27. Korsmeyer R W, Gurny R, Doelker E, Buri P, Peppas N A. Mechanisms of solute release from porous hydrophilic polymers. Int J Pharm [Internet]. 1983 May 1 [cited 2019 Apr. 27]; 15(1):25-35.

28. Peppas N A. Analysis of Fickian and non-Fickian drug release from polymers. Pharm Acta Helv [Internet]. 1985 January [cited 2015 Apr. 23]; 60(4):110-1.
29. CHMP. Committee for Medicinal Products for Human Use (CHMP) Assessment report [Internet]. 2014 [cited 2020 Dec. 23].
30. Zhu M, Wang J, Li N. A novel thermo-sensitive hydrogel-based on poly(N-isopropylacrylamide)/hyaluronic acid of ketoconazole for ophthalmic delivery. Artif Cells, Nanomedicine Biotechnol. 2018; 46(6):1282-7.
31. Ammar H O, Salama H A, Ghorab M, Mahmoud A A. Nanoemulsion as a Potential Ophthalmic Delivery System for Dorzolamide Hydrochloride. AAPS PharmSciTech. 2009; 10(3):808-19.
32. Draize J H, Woodard G, Calvery H O. Methods for the study of irritation and toxicity of substances applied topically to the skin and mucous membranes. J Pharmacol Exp Ther [Internet]. 1944 [cited 2020 Nov. 11]; 82:377-90.
33. Danaei M, Dehghankhold M, Ataei S, Hasanzadeh Davarani F, Javanmard R, Dokhani A, et al. Impact of Particle Size and Polydispersity Index on the Clinical Applications of Lipidic Nanocarrier Systems. Pharmaceutics. 2018; 10(2):57.
34. Harbi I, Aljaeid B, El-Say K M, Zidan A S. Glycosylated Sertraline-Loaded Liposomes for Brain Targeting: QbD Study of Formulation Variabilities and Brain Transport. AAPS PharmSciTech. 2016; 17(6):1404-20.
35. Ahmed T A. Development of rosuvastatin flexible lipid-based nanoparticles: Promising nanocarriers for improving intestinal cells cytotoxicity. BMC Pharmacol Toxicol. 2020 Feb. 21; 21(1).
36. Alomrani A H, Shazly G A, Amara A A A F, Badran M M. Itraconazole-hydroxypropyl-β-cyclodextrin loaded deformable liposomes: In vitro skin penetration studies and antifungal efficacy using Candida albicans as model. Colloids Surfaces B Biointerfaces [Internet]. 2014 Sep. 1 [cited 2020 Nov. 16]; 121:74-81.
37. Abdellatif M M, Khalil I A, Khalil M A F. Sertaconazole nitrate loaded nanovesicular systems for targeting skin fungal infection: In-vitro, ex-vivo and in-vivo evaluation. Int J Pharm [Internet]. 2017 Jul. 15 [cited 2020 Nov. 16]; 527(1-2):1-11.
38. Raghuwanshi S, Kadu B S. Transdermal delivery of Etoricoxib through ethosomal formulation: An ingenious approach towards treatment of skin inflammation. J Drug Deliv Sci Technol [Internet]. 2017 Aug. 1 [cited 2020 Nov. 16]; 40:95-104.
39. Tabandeh H, Mortazavi S A. An Investigation into Some Effective Factors on Encapsulation Efficiency of Alpha-Tocopherol in MLVs and the Release Profile from the Corresponding Liposomal Gel. Iran J Pharm Res UPR [Internet]. 2013 [cited 2020 Nov. 16]; 12(Suppl):21-30.
40. Ahmed T A. Preparation of transfersomes encapsulating sildenafil aimed for transdermal drug delivery: Plackett-Burman design and characterization. J Liposome Res [Internet]. 2015; 25(1):1-10.
41. Perez A P, Altube M J, Schilrreff P, Apezteguia G, Celes F S, Zacchino S, et al. Topical amphotericin B in ultra-deformable liposomes: Formulation, skin penetration study, antifungal and antileishmanial activity in vitro. Colloids Surfaces B Biointerfaces. 2016; 139:190-8.
42. Jain S, Tiwary A K, Sapra B, Jain N K. Formulation and evaluation of ethosomes for transdermal delivery of lamivudine. AAPS PharmSciTech. 2007; 8(4):E111.
43. Das S, Chaudhury A. Recent advances in lipid nanoparticle formulations with solid matrix for oral drug delivery [Internet]. Vol. 12, AAPS PharmSciTech. Springer; 2011 [cited 2020 Nov. 16]. p. 62-76.
44. Ahmed T A, El-Say K M. Transdermal film-loaded finasteride microplates to enhance drug skin permeation: Two-step optimization study. Eur J Pharm Sci [Internet]. 2016; 88:246-56.
45. Owusu-Ware S K, Chowdhry B Z, Leharne S A, Antonijević M D. Phase behaviour of dehydrated phosphatidylcholines. J Therm Anal calorim. 2017; 127(1):415-21.
46. Nzai J M, Proctor A. Determination of phospholipids in vegetable oil by fourier transform infrared spectroscopy. JAOCS, J Am Oil Chem Soc. 1998; 75(10):1281-9.
47. Zidan A S, Spinks C, Fortunak J, Habib M, Khan M A. Near-infrared investigations of novel anti-HIV tenofovir liposomes. AAPS J. 2010; 12(2):202-14.
48. Mascaro V L D M, Hofling-Lima A L, Gompertz O F, Yu M C Z, Matta D A da, Colombo A L. Antifungal susceptibility testing of yeast isolated from corneal infections. Arq Bras Oftalmol. 2003; 66(5):647-52.
49. Rajas N J, Gounder T, Mani T. Review Article I N SITU OPTHALMIC GELS: A DEVELOPING TREND. Internatinal J Pharm Sci Rev abd Res. 2011; 7(1):8-14.
50. Song J, Bi H, Xie X, Guo J, Wang X, Liu D. Preparation and evaluation of sinomenine hydrochloride in situ gel for uveitis treatment. Int Immunopharmacol. 2013 Sep. 1; 17(1):99-107.
51. Gaudana R, Ananthula H K, Parenky A, Mitra A K. Ocular drug delivery. AAPS J [Internet]. 2010 September [cited 2016 Sep. 19]; 12(3):348-60.
52. Jaiswal M, Kumar M, Pathak K. Zero order delivery of itraconazole via polymeric micelles incorporated in situ ocular gel for the management of fungal keratitis. Colloids Surfaces B Biointerfaces [Internet]. 2015; 130:23-30.
53. Lynch C R, Kondiah P P D, Choonara Y E, du Toit L C, Ally N, Pillay V. Hydrogel Biomaterials for Application in Ocular Drug Delivery [Internet]. Vol. 8, Frontiers in Bioengineering and Biotechnology. Frontiers Media S.A.; 2020 [cited 2020 Dec. 21].
54. Wu Y, Liu Y, Li X, Kebebe D, Zhang B, Ren J, et al. Research progress of in-situ gelling ophthalmic drug delivery system. Asian J Pharm Sci [Internet]. 2019; 14(1):1-15.
55. Vigani B, Rossi S, Sandri G, Bonferoni M C, Caramella C M, Ferrari F. Recent advances in the development of in situ gelling drug delivery systems for non-parenteral administration routes. Pharmaceutics. 2020; 12(9):1-29.
56. Sheshala R, Kok Y, Ng J, Thakur R, Dua K. In Situ Gelling Ophthalmic Drug Delivery System: An Overview and Its Applications. Recent Pat Drug Deliv Formul [Internet]. 2015 Sep. 16 [cited 2020 Nov. 23]; 9(3):242-53.
57. Kakkar S, Karuppayil S M, Raut J S, Giansanti F, Papucci L, Schiavone N, et al. Lipid-polyethylene glycol based nano-ocular formulation of ketoconazole. Int J Pharm. 2015; 495:276-89.
58. Roggeband R, York M, Pericoi M, Braun W. Eye irritation responses in rabbit and man after single applications of equal volumes of undiluted model liquid detergent products. Food Chem Toxicol [Internet]. 2000 August [cited 2020 Nov. 23]; 38(8):727-34.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An in situ gelling composition, comprising:
   an ophthalmic formulation comprising transethosomes, wherein the transethosomes comprise
   a phospholipid layer;
   an edge activator;
   ethanol incorporated within the phospholipid layer; and
   ketoconazole,
   wherein a surface of the transethosome is modified with a cationic charge inducing agent; and
   a gelling agent.

2. The in situ gelling composition of claim 1, wherein the phospholipid is L-α-phosphatidylcholine and the edge activator is polysorbate-80.

3. The in situ gelling composition of claim 1, wherein the cationic charge inducing agent is stearyl amine.

4. The in situ gelling composition of claim 3, wherein the stearyl amine is present in an amount of 10-20% w/w.

5. The in situ gelling composition of claim 1, wherein the edge activator is present in an amount of 10-25% w/w of total lipid.

6. The in situ gelling composition of claim 1, wherein the ethanol is present in a hydration medium in an amount of 12-50% v/v.

7. The in situ gelling composition of claim 1, wherein a ketoconazole to phospholipid molar ratio is from 1:2 to 1:4.

8. The in situ gelling composition of claim 1, wherein the ketoconazole is present in an amount of 0.05-0.2% w/v.

9. The in situ gelling composition of claim 1, wherein the transethosomes have an average diameter of 130-170 nm.

10. The in situ gelling composition of claim 1, wherein the transethosomes have a zeta potential value of +30-40 mV.

11. The in situ gelling composition of claim 1, wherein the composition further comprises hydroxypropyl methylcellulose (HPMC).

12. The in situ gelling composition of claim 11, wherein the HPMC is present in an amount of 0.2-0.8% w/v.

13. The in situ gelling composition of claim 1, wherein the gelling agent is selected from the group consisting of sodium alginate, poloxamer 407, and prop-2-enoic acid.

14. The in situ gelling composition of claim 13, wherein gelling agent is prop-2-enoic acid and wherein the gelling agent is present in an amount of 0.05-1.5% w/v.

15. A method for the sustained delivery of ketoconazole to a posterior eye segment of a subject in need thereof, comprising ocularly administering a therapeutically effective amount of the in situ gelling composition of claim 1 to the subject.

16. The method of claim 15, wherein the subject has a fungal eye infection in the posterior eye segment.

* * * * *